United States Patent
Sjölund et al.

(10) Patent No.: US 10,762,398 B2
(45) Date of Patent: Sep. 1, 2020

(54) MODALITY-AGNOSTIC METHOD FOR MEDICAL IMAGE REPRESENTATION

(71) Applicant: Elekta AB, Stockholm (SE)

(72) Inventors: Jens Olof Sjölund, Stockholm (SE); Jonas Anders Adler, Stockholm (SE)

(73) Assignee: Elekta AB, Stockholm (SE)

( * ) Notice: Subject to any disclaimer, the term of this patent is extended or adjusted under 35 U.S.C. 154(b) by 184 days.

(21) Appl. No.: 15/986,065

(22) Filed: May 22, 2018

(65) Prior Publication Data

US 2019/0332900 A1 Oct. 31, 2019

Related U.S. Application Data

(60) Provisional application No. 62/664,879, filed on Apr. 30, 2018.

(51) Int. Cl.
*G06K 9/62* (2006.01)
*A61N 5/10* (2006.01)
(Continued)

(52) U.S. Cl.
CPC ......... *G06K 9/6289* (2013.01); *A61N 5/1039* (2013.01); *G06N 3/08* (2013.01);
(Continued)

(58) Field of Classification Search
CPC ...... G06K 9/6256; G06K 9/66; G06K 9/6267; G06K 2009/4666; G06K 2209/05;
(Continued)

(56) References Cited

U.S. PATENT DOCUMENTS

| | | |
|---|---|---|
| 2013/0211230 A1 | 8/2013 | Sperling |
| 2017/0345140 A1* | 11/2017 | Zhang ................... G06T 7/0004 |
| 2019/0120918 A1* | 4/2019 | Pereira ................ A61B 5/7267 |

FOREIGN PATENT DOCUMENTS

| | | |
|---|---|---|
| CN | 103049895 A | 4/2013 |
| CN | 103126702 A | 6/2013 |

(Continued)

OTHER PUBLICATIONS

"International Application Serial No. PCT/EP2019/061117, International Search Report dated Aug. 1, 2019", 5 pgs.
"International Application Serial No. PCT/EP2019/061117, Written Opinion dated Aug. 1, 2019", 10 pgs.
James, Alex Pappachen, et al., "Medical image fusion: A survey of the state of the art", Information Fusion, Elsevier, US, vol. 19, (Jan. 8, 2014), 45 pgs.

(Continued)

*Primary Examiner* — Ajibola A Akinyemi
(74) *Attorney, Agent, or Firm* — Schwegman Lundberg & Woessner, P.A.

(57) ABSTRACT

Techniques for the operation and use of a model that learns the general representation of multimodal images is disclosed. In various examples, methods from representation learning are used to find a common basis for representation of medical images. These include aspects of encoding, fusion, and downstream tasks, with use of the general representation and model. In an example, a method for generating a modality-agnostic model includes receiving imaging data, encoding the imaging data by mapping data to a latent representation, fusing the encoded data to conserve latent variables corresponding to the latent representation, and training a model using the latent representation. In an example, a method for processing imaging data using a trained modality-agnostic model includes receiving imaging data, encoding the data to the defined encoding, processing the encoded data with a trained model, and performing imaging processing operations based on output of the trained model.

31 Claims, 11 Drawing Sheets

(51) Int. Cl.
*G06N 3/08* (2006.01)
*G06T 11/00* (2006.01)
*G06N 3/04* (2006.01)
*G06T 7/174* (2017.01)
*H04N 19/176* (2014.01)
*G06T 7/11* (2017.01)

(52) U.S. Cl.
CPC ........... *G06K 2209/05* (2013.01); *G06N 3/04* (2013.01); *G06T 7/11* (2017.01); *G06T 7/174* (2017.01); *G06T 11/003* (2013.01); *G06T 2207/10072* (2013.01); *G06T 2207/20081* (2013.01); *G06T 2207/20084* (2013.01); *H04N 19/176* (2014.11)

(58) Field of Classification Search
CPC .... G06K 9/00791; G06K 9/52; G06K 9/6289; G06K 2209/01; G06K 9/00214; G06K 9/3241; G06K 9/4609; G06K 9/4619; G06K 9/6247; G06K 9/6269; G06K 2209/051; G06K 9/00; G06K 9/00281; G06K 9/00335
USPC ....................................................... 382/131
See application file for complete search history.

(56) References Cited

FOREIGN PATENT DOCUMENTS

| CN | 103617605 A | 3/2014 |
|---|---|---|
| CN | 104182954 A | 12/2014 |

OTHER PUBLICATIONS

Joyce, Thomas, et al., "Robust Multi-modal MR Image Synthesis", Serious Games; [Lecture Notes in Computer Science; Lect.Notes Computer], Springer International Publishing, Cham, Page(S), (Sep. 4, 2017), 8 pgs.

Chartsias, Agisilaos, et al., "Multimodal MR Synthesis via Modality-Invariant Latent Representation", IEEE Transactions on Medical Imaging, vol. 37, No. 3 0278-0062, (Jan. 2017), 12 pgs.

Havaei, Mohammad, et al., "HeMIS: Hetero-Modal Image Segmentation", MICCAI 2016, Part II, LNCS 9901, (2016), 469-477.

Huang, Y., et al., "Cross-Modality Image Synthesis via Weakly-Coupled and Geometry Co-Regularized Joint Dictionary Learning", IEEE Transactions on Medical Imaging 37 (3)., (2017), 14 pgs.

Kingma, Diederik P, et al., "Auto-Encoding Variational Bayes", arXiv:1312.6114v10, (2014), 14 pgs.

Varsavsky, Thomas, et al., "PIMMS: Permutation Invariant Multi-Modal Segmentation", 1st Conference on Medical Imaging with Deep Learning (MIDL 2018), Amsterdam, The Netherlands, (2018), 9 pgs.

* cited by examiner

US 10,762,398 B2

MODALITY-AGNOSTIC METHOD FOR MEDICAL IMAGE REPRESENTATION

PRIORITY CLAIM

This application claims the benefit of priority to U.S. Application Ser. No. 62/664,879, filed Apr. 30, 2018, which is incorporated herein by reference in its entirety.

TECHNICAL FIELD

Embodiments of the present disclosure pertain generally to medical data and artificial intelligence image processing techniques. In particular, the present disclosure pertains to the generation, training, and use of neural networks adapted for processing imaging data from among multiple types and mode variations of imaging modalities, including with uses for medical imaging processing and radiotherapy treatment system operations.

BACKGROUND

In medicine in general, and in radiotherapy in particular, medical imaging is used to probe the interior of the body to obtain information about the interior without having to physically enter the body using surgery or other invasive mechanisms. In general, the body can be described as a spatial (and possibly also temporal) distribution of a large set of parameters. For example, one point represented by an imaging unit (e.g., a voxel) might have density 1.2 g/mm$^3$, contain 80% water, 20% fat, have a $^{18}$F uptake of 5 MBq/mL, temperature 38° C., contain 5000 glioblastoma cells/mm$^3$, etc. The goal of medical imaging is to estimate one or more of these parameters. However, any particular imaging modality can only determine a very small number of these parameters. For example, CT can only determine the radiological density (which roughly correlates with density), PET can only determine radionuclei uptake, etc. It has therefore become increasingly common to combine several imaging modalities during treatment planning and treatment administration.

Most state-of-the-art methods for machine learning in medical imaging can be summarized as function approximation; training data consisting of input-output pairs of some type (e.g. CT-images with segmentations) are acquired from, for instance, expert clinicians and a function is "trained" to approximate this mapping. Popular methods involve, for example, neural networks. In these methods, a set of parametrized functions $f_\theta$ are selected, where $\theta$ is a set of parameters (e.g. convolution kernels and biases) that are selected by minimizing the average error over the training data. If the input-output pairs are denoted by $(x_i, y_i)$, this can be formalized by solving a minimization problem such as $$\min_\theta \sum_i \|f_\theta(x_i) - y_i\|_2^2$$

Once the network has been trained (i.e. $\theta$ has been selected), the function $f_\theta$ can be applied to any new input. For example, in the above setting of segmentation of CT images a never-before-seen CT image can be fed into $f_\theta$, and with the objective to obtain a segmentation that matches what an expert clinician would find.

In classical machine learning methods, however, the function $f_\theta$ only takes input of some fixed type, e.g. CT-images or PET images. If a method is desired to be trained using both CT and PET images as input, the whole training process has to be re-done. Given that the current trend is an ever-increasing number of imaging modalities being used, in new and original combinations, a combinatorial expansion of data may result. For instance, with 2 imaging modalities there are 3 ways to combine them (either or both), but with 5 modalities there are 31 combinations, and with 10 modalities there are more than 1000 combinations.

Overview

The present disclosure includes procedures to develop and utilize methods of processing and representing imaging data from among multiple imaging formats, source modalities, and modality operation parameters. In various examples, these processing and representation techniques utilize using artificial intelligence (AI) processing techniques, including neural networks (NNs) and other forms of machine learning (ML) implementations. The present disclosure specifically discusses methods from so called "representation learning" or "feature learning" in order to find a common basis for the representation of medical images. The common representation can then be used as input to the function $f_\theta$ as used in any number of machine learning methods and minimization problems.

The following includes a number of illustrative examples relevant to the use of radiotherapy imaging processing in the context of radiotherapy planning and treatment. However, it will be apparent that the presently described use and analysis of imaging data may be incorporated into other medical imaging workflows used for a variety of planning, diagnostic, evaluative, interpretative, or treatment settings.

The present disclosure of a neural network model is provided as an example of a modality-agnostic imaging processing model that learns the general representation of medical images (e.g., MRI images, CT images, etc., or variations within types of such imaging) in an unsupervised manner. The network is trained using a fusion of data from this general representation in a latent space, to result in a network configuration that can be considered as insensitive to missing models or training data sets. This fused latent representation of data may then be used for a number of further processing purposes in connection with radiotherapy imaging processing and medical imaging workflows. The present disclosure also includes examples of encoder models (including variational autoencoder models implemented by a neural network) used in connection generating a fused representation for an imaging processing model. Accordingly, the presently described models provide improved results for a variety of imaging processing purposes such as reconstruction, segmentation, and other image processing aspects which may have missing or incomplete data or modeling.

In an example, computer implemented method for generating a modality-agnostic image processing model, includes operations comprising: receiving imaging data from multiple imaging modalities; encoding the imaging data based on a defined data encoding, by mapping the imaging data to respective latent representations; fusing the encoded imaging data, by mapping the respective latent representations to a fused latent representation of the encoded imaging data, such that the mapping conserves respective latent variables corresponding to a spatial representation of the respective latent representations; training a model for medical imaging processing, using the fused latent representation of the encoded imaging data; and outputting the trained model, the model adapted to produce an output from subsequent medical imaging data according to the training using the fused latent representation. As discussed in the further examples below, the encoding may be performed with a variational autoencoder model, and the fused latent representation may be produced as a fused representation image, among other variations. In particular, the output produced from operating the trained model may be used for performing a variety of radiotherapy planning operations.

In an example, a computer-implemented method for processing imaging data using a trained modality-agnostic model, includes operations comprising: receiving medical imaging data of a first imaging modality; encoding the medical imaging data based on a defined data encoding, by mapping the medical imaging data to a latent representation; processing the encoded medical imaging data with a trained model, such that the trained model produces an output based on the latent representation, based on training of the model to a fused latent representation of the imaging data, where the training of the model is performed based on a mapping of a latent representation from at least a second imaging modality; and performing an image processing operation on the medical imaging data based on the output produced by the trained model. As discussed in the further examples below, the image processing operation may involve at least one of: segmentation, denoising, synthesis, classification, regression, or reconstruction operations.

In an example, a system (e.g., a computing system) for operation of a modality-agnostic imaging processing model, includes: processing circuitry comprising at least one processor; and a storage medium comprising instructions, which when executed by the at least one processor, cause the processor to: process imaging data produced from a medical imaging modality; encode the imaging data to a latent representation based on a defined data encoding; perform mapping of the encoded imaging data to a common latent representation, that conserves respective latent variables corresponding to a spatial representation of the latent representation; train a model for medical imaging processing, using the common latent representation; and utilize the trained model to produce an output from subsequent medical imaging data, in connection with an image processing operation. As discussed in the further examples below, the imaging data may be produced from at least one: Magnetic resonance imaging (MRI), computed tomography (CT), Positron Emission Tomography (PET), PET-CT, Ultrasound, X-Ray, Fluoroscopy, Single-photon emission computed tomography (SPECT), Elastography, Photoacoustic, Magnetoencephalography (MEG), or Electroencephalography (EEG) imaging procedure, or combinations of such imaging procedures. In a specific example, the imaging procedure involves a MRI imaging procedure that operates in at least one type of MRI imaging mode, such that the MRI imaging mode produces at least one of: T1, T1 with contrast, T2, PD, SSFP, STIR, FLAIR, DIR, DWI, PWI, or fMRI images.

The examples described herein may be implemented in a variety of embodiments. For example, one embodiment includes a computing device including processing hardware (e.g., a processor or other processing circuitry) and memory hardware (e.g., a storage device or volatile memory) including instructions embodied thereon, such that the instructions, which when executed by the processing hardware, cause the computing device to implement, perform, or coordinate the electronic operations for these techniques and system configurations. Another embodiment discussed herein includes a computer program product, such as may be embodied by a machine-readable medium or other storage device, which provides the instructions to implement, perform, or coordinate the electronic operations for these techniques and system configurations. Another embodiment discussed herein includes a method operable on processing hardware of the computing device, to implement, perform, or coordinate the electronic operations for these techniques and system configurations.

In further embodiments, the logic, commands, or instructions that implement aspects of the electronic operations described above, may be provided in a distributed or centralized computing system, including any number of form factors for the computing system such as desktop or notebook personal computers, mobile devices such as tablets, netbooks, and smartphones, client terminals and server-hosted machine instances, and the like. Another embodiment discussed herein includes the incorporation of the techniques discussed herein into other forms, including into other forms of programmed logic, hardware configurations, or specialized components or modules, including an apparatus with respective means to perform the functions of such techniques. The respective algorithms used to implement the functions of such techniques may include a sequence of some or all of the electronic operations described above, or other aspects depicted in the accompanying drawings and detailed description below.

The above overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example but not by way of limitation, various embodiments discussed in the present document.

DETAILED DESCRIPTION

Figure 1:
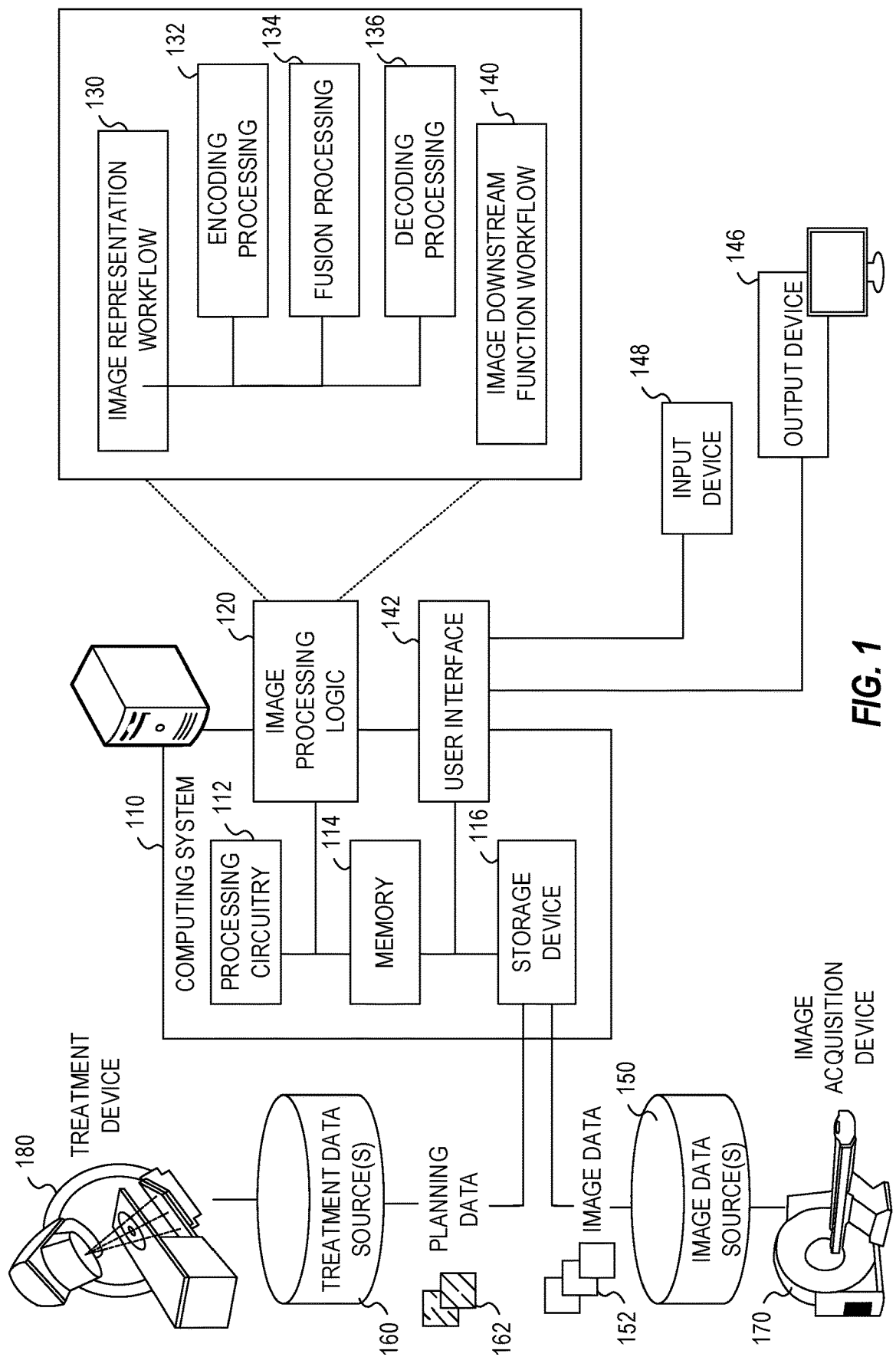
FIG. 1 illustrates an exemplary radiotherapy system adapted for performing medical imaging processing.

In the following detailed description, reference is made to the accompanying drawings which form a part hereof, and which is shown by way of illustration-specific embodiments in which the present invention may be practiced. These embodiments, which are also referred to herein as "examples," are described in sufficient detail to enable those skilled in the art to practice the invention, and it is to be understood that the embodiments may be combined, or that other embodiments may be utilized and that structural, logical and electrical changes may be made without departing from the scope of the present invention. The following detailed description is, therefore, not be taken in a limiting sense, and the scope of the present invention is defined by the appended claims and their equivalents.

The present disclosure includes various techniques involving the training, configuration, operation, and use of an image processing model (e.g., a neural network model) that learns a general representation of multimodal imaging data in an unsupervised manner. This model is designed to be insensitive to missing imaging modalities, and thus is adaptable to apply trained concepts to images of a second modality output even if trained on images from a first modality output. With the use of a latent representation, small amounts of labeled data may be used to train the neural network for purposes such as anatomical feature segmentation, in order to support automatic segmentation and other image processing actions during the treatment planning of various types of radiotherapy treatments.

Given the many combinations of imaging types (e.g., MR, CT, PET, etc.), and different operational modes or parameters within a single imaging type (such as T1, T2, T1 with contrast, and Flair as different MR operational modes), techniques are needed to efficiently consider the information from all available imaging types without needing an exponential amount of training data. Patient artifacts, modality variations, and other factors make automatic segmentation and other image processing functions difficult to be used in many clinical settings from accurate training. In particular, one of the significant challenges is to obtain data for training all paths of a trained model. Missing training data from one or more modality types or modality modes is common, and because the very first layer in neural network considers values from all channels, missing models may result in a bias in the computation in the network.

Limited approaches have been suggested for handling missing data in medical imaging, including retraining a specific model to handle missing modalities or synthesizing such missing data. As another example, one approach has proposed the use of different networks trained on different combination of contrasts, whereas another approach has proposed the use of hetero-modal tumor segmentation for missing modalities through a fusion of imaging data representations. Other approaches involving neural networks commonly require labeled data and the processing of labeling the data for supervised learning, and as a result, are labor intensive and time consuming. In fact, current practical applications of deep learning methods mostly focus on results derived from supervised training, which involves a large amount of labeled data to train the network.

In the medical field, one of the primary reasons of why it is hard to collect huge amount of data is the domain complexity. Recent research has proposed use of supervised multimodal neural networks for automatic brain tumor segmentation in connection with radiotherapy treatment of the tumor, but such neural networks often need paramount labelled data to result in proper generalization. However, labeling tumors in brain MR imaging accurately, for example, requires a high level of expertise and knowledge and thus a supervised neural network will require a very large amount of labeled data to achieve favorable results. Further, such neural networks are usually trained for specific tasks, on a specific type of input, and often do not provide a generalization of learned concepts.

In an example disclosed herein, an encoding step of a processing technique is used to map each input datum to a shared latent representation. This is followed by a fusion step, in which all the resulting data points are reduced to a single data point. This produces a unified representation. By passing the unified representation through a decoding step, the input data can be (approximately) reconstructed. The main requirement on the fusion step is that the fusion operation take a variable number of input points and reduce them to a single point. Simple functions capable of this include the mean and the maximum, but other functions may be employed.

As further discussed, the unified representation can be used as input to the function $f_\theta$ for neural network training or inferences (e.g., prediction, or usage). For instance, this function may correspond to an auxiliary task such as segmentation, denoising, or reconstruction of something other than the input data. As a result, even when only small amounts of data are available for the auxiliary task, the presently disclosed techniques can help improve the performance of the neural network by leveraging information from the unified representation that has been learned on other tasks. In other words, the method can be used for semi-supervised learning of the neural network.

In further examples, it may be necessary to enforce some type of regularity (e.g. smoothness) of the latent representation, which can be done using, for instance, a variational autoencoder for modality-generic processing. Further techniques are disclosed herein for the configuration, use, and output of such variational autoencoders, and the fashion in which encoding and decoding from a variational autoencoder may be used to map to a latent space for multiple types or modes of modalities.

Variations to the following exemplary implementations will be apparent from the following disclosure. For instance, the encoding and decoding operations disclosed herein may be designed to be specific to a particular modality or imaging type or characteristic. However, the use of generic encoding and decoding operations enable the application of the trained model to a previously unseen type of input modality, if the new input modality is sufficiently similar to those used in the training. Further, the following exemplary implementations of the encoding and decoding steps are described with use of a neural network, but other choices of processing algorithms are usable. Accordingly, the following infrastructure enables a flexible approach for training, processing, and outputting in suitable variations of imaging data types.

FIG. 1 illustrates an exemplary radiotherapy system adapted to perform radiotherapy image processing operations using one or more of the approaches discussed herein. These radiotherapy image processing operations are performed to enable the radiotherapy system to provide radiation therapy to a patient based on specific aspects of captured medical imaging data. Specifically, the following processing operations may be implemented as part of an image representation workflow 130 and an image downstream function workflow 140, implemented by image processing logic 120. It will be understood, however, that many variations and use cases of the following trained models and image processing logic 120 may be provided, including in data verification, visualization, and other medical evaluative and diagnostic settings.

The radiotherapy system includes a radiotherapy processing computing system 110 which hosts image processing logic 120. The radiotherapy processing computing system 110 may be connected to a network (not shown), and such network may be connected to the Internet. For instance, a network can connect the radiotherapy processing computing system 110 with one or more medical information sources (e.g., a radiology information system (RIS), a medical record system (e.g., an electronic medical record (EMR)/electronic health record (EHR) system), an oncology information system (OIS)), one or more image data sources 150, an image acquisition device 170 (e.g., an imaging modality), a treatment device 180 (e.g., a radiation therapy device), and a treatment data source 160. As an example, the radiotherapy processing computing system 110 can be configured to perform treatment plan design, generation, and implementation by executing instructions or data in connection with the image processing logic 120, as part of operations to generate and customize radiation therapy treatment plans to be used by the treatment device 180.

The radiotherapy processing computing system 110 may include processing circuitry 112, memory 114, a storage device 116, and other hardware and software-operable features such as a user interface 142, a communication interface (not shown), and the like. The storage device 116 may store computer-executable instructions, such as an operating system, radiation therapy treatment plans, software programs (e.g., radiotherapy treatment plan software, image or anatomical visualization software, AI implementations and algorithms such as provided by DL models, ML models, and neural networks, etc.), and any other computer-executable instructions to be executed by the processing circuitry 112.

In an example, the processing circuitry 112 may include a processing device, such as one or more general-purpose processing devices such as a microprocessor, a central processing unit (CPU), a graphics processing unit (GPU), an accelerated processing unit (APU), or the like. More particularly, the processing circuitry 112 may be a complex instruction set computing (CISC) microprocessor, a reduced instruction set computing (RISC) microprocessor, a very long instruction Word (VLIW) microprocessor, a processor implementing other instruction sets, or processors implementing a combination of instruction sets. The processing circuitry 112 may also be implemented by one or more special-purpose processing devices such as an application specific integrated circuit (ASIC), a field programmable gate array (FPGA), a digital signal processor (DSP), a System on a Chip (SoC), or the like. As would be appreciated by those skilled in the art, in some examples, the processing circuitry 112 may be a special-purpose processor, rather than a general-purpose processor. The processing circuitry 112 may include one or more known processing devices, such as a microprocessor from the Pentium™, Core™, Xeon™, or Itanium® family manufactured by Intel™, the Turion™, Athlon™, Sempron™, Opteron™, FX™, Phenom™ family manufactured by AMD™, or any of various processors manufactured by Sun Microsystems. The processing circuitry 112 may also include graphical processing units such as a GPU from the GeForce®, Quadro®, Tesla® family manufactured by Nvidia™, GMA, Iris™ family manufactured by Intel™, or the Radeon™ family manufactured by AMD™. The processing circuitry 112 may also include accelerated processing units such as the Xeon Phi™ family manufactured by Intel™. The disclosed embodiments are not limited to any type of processor(s) otherwise configured to meet the computing demands of identifying, analyzing, maintaining, generating, and/or providing large amounts of data or manipulating such data to perform the methods disclosed herein. In addition, the term "processor" may include more than one processor, for example, a multi-core design or a plurality of processors each having a multi-core design. The processing circuitry 112 can execute sequences of computer program instructions, stored in memory 114, and accessed from the storage device 116, to perform various operations, processes, methods that will be explained in greater detail below.

The memory 114 may comprise read-only memory (ROM), a phase-change random access memory (PRAM), a static random access memory (SRAM), a flash memory, a random access memory (RAM), a dynamic random access memory (DRAM) such as synchronous DRAM (SDRAM), an electrically erasable programmable read-only memory (EEPROM), a static memory (e.g., flash memory, flash disk, static random access memory) as well as other types of random access memories, a cache, a register, a compact disc read-only memory (CD-ROM), a digital versatile disc (DVD) or other optical storage, a cassette tape, other magnetic storage device, or any other non-transitory medium that may be used to store information including image, data, or computer executable instructions (e.g., stored in any format) capable of being accessed by the processing circuitry 112, or any other type of computer device. For instance, the computer program instructions can be accessed by the processing circuitry 112, read from the ROM, or any other suitable memory location, and loaded into the RAM for execution by the processing circuitry 112.

The storage device 116 may constitute a drive unit that includes a machine-readable medium on which is stored one or more sets of instructions and data structures (e.g., software) embodying or utilized by any one or more of the methodologies or functions described herein (including, in various examples, the image processing logic 120 and the user interface 142). The instructions may also reside, completely or at least partially, within the memory 114 and/or within the processing circuitry 112 during execution thereof by the radiotherapy processing computing system 110, with the memory 114 and the processing circuitry 112 also constituting machine-readable media.

The memory device 114 and the storage device 116 may constitute a non-transitory computer-readable medium. For example, the memory device 114 and the storage device 116 may store or load instructions for one or more software applications on the computer-readable medium. Software applications stored or loaded with the memory device 114 and the storage device 116 may include, for example, an operating system for common computer systems as well as for software-controlled devices. The radiotherapy processing computing system 110 may also operate a variety of software programs comprising software code for implementing the image processing logic 120 and the user interface 142. Further, the memory device 114 and the storage device 116 may store or load an entire software application, part of a software application, or code or data that is associated with a software application, which is executable by the processing circuitry 112. In a further example, the memory device 114 and the storage device 116 may store, load, and manipulate one or more radiation therapy treatment plans, imaging data, segmentation data, treatment visualizations, histograms or measurements, AI model data (e.g., weights and parameters), labels and mapping data, etc. It is contemplated that software programs may be stored not only on the storage device 116 and the memory 114 but also on a removable computer medium, such as a hard drive, a computer disk, a CD-ROM, a DVD, a Blu-Ray DVD, USB flash drive, a SD card, a memory stick, or any other suitable medium; such software programs may also be communicated or received over a network.

Although not depicted, the radiotherapy processing computing system 110 may include a communication interface, network interface card, and communications circuitry. An example communication interface may include, for example, a network adaptor, a cable connector, a serial connector, a USB connector, a parallel connector, a high-speed data transmission adaptor (e.g., such as fiber, USB 3.0, thunderbolt, and the like), a wireless network adaptor (e.g., such as a IEEE 802.11/Wi-Fi adapter), a telecommunication adapter (e.g., to communicate with 3G, 4G/LTE, and 5G, networks and the like), and the like. Such a communication interface may include one or more digital and/or analog communication devices that permit a machine to communicate with other machines and devices, such as remotely located components, via a network. The network may provide the functionality of a local area network (LAN), a wireless network, a cloud computing environment (e.g., software as a service, platform as a service, infrastructure as a service, etc.), a client-server, a wide area network (WAN), and the like. For example, network may be a LAN or a WAN that may include other systems (including additional image processing computing systems or image-based components associated with medical imaging or radiotherapy operations).

In an example, the radiotherapy processing computing system 110 may obtain image data 152 from the image data source 150, for hosting on the storage device 116 and the memory 114. The storage device 116 and memory 114 may store and host data to perform a variety of purposes, including the image data 152, patient data, and other data required to create and implement a radiation therapy treatment plan and associated segmentation (or other image processing) operations.

The processing circuitry 112 may be communicatively coupled to the memory 114 and the storage device 116, and the processing circuitry 112 may be configured to execute computer executable instructions stored thereon from either the memory 114 or the storage device 116. The processing circuitry 112 may execute instructions to cause medical images from the image data 152 to be received or obtained in memory 114, and processed using the image processing logic 120. For example, the radiotherapy processing computing system 110 may receive image data 152 from the image acquisition device 170 or image data sources 150 via a communication interface and network to be stored or cached in the storage device 116. The processing circuitry 112 may also send or update medical images stored in memory 114 or the storage device 116 via a communication interface to another database or data store (e.g., a medical facility database). In some examples, one or more of the systems may form a distributed computing or virtualized environment that uses a network to collaboratively perform the embodiments described herein. In addition, such network may be connected to internet to communicate with servers and clients that reside remotely on the internet.

In an example, the image data 152 may include one or more MRI image (e.g., 2D MRI, 3D MRI, 2D streaming MRI, 4D MRI, 4D volumetric MRI, 4D cine MRI, etc.), functional MRI images (e.g., fMRI, DCE-MRI, diffusion MRI), Computed Tomography (CT) images (e.g., 2D CT, Cone beam CT, 3D CT, 4D CT), ultrasound images (e.g., 2D ultrasound, 3D ultrasound, 4D ultrasound), Positron Emission Tomography (PET) images, PET-CT images, X-ray images, fluoroscopic images, radiotherapy portal images, Single-Photo Emission Computed Tomography (SPECT) images, Elastography images, Photoacoustic images, Magnetoencephalography (MEG) images, Electroencephalography (EEG) images, or computer generated synthetic images (e.g., pseudo-CT images) and the like. Further, the image data 152 may also include or be associated with medical image processing data, for instance, training images, and ground truth images, contoured images, and dose images. In other examples, an equivalent representation of an anatomical area may be represented in non-image formats (e.g., coordinates, mappings, etc.).

In an example, the image data 152 may be received from the image acquisition device 170 and stored in one or more of the image data sources 150 (e.g., a Picture Archiving and Communication System (PACS), a Vendor Neutral Archive (VNA), a medical record or information system, a data warehouse, etc.). Accordingly, the image acquisition device 170 may comprise a MRI imaging device, a CT imaging device, a PET imaging device, an ultrasound imaging device, a fluoroscopic device, a SPECT imaging device, an integrated Linear Accelerator and MRI imaging device, or other medical imaging devices for obtaining the medical images of the patient. The image data 152 may be received and stored in any type of data or any type of format (e.g., in a Digital Imaging and Communications in Medicine (DICOM) format) that the image acquisition device 170 and the radiotherapy processing computing system 110 may use to perform operations consistent with the disclosed embodiments. Further, in some examples, the models discussed herein may be trained to process the original image data format or a derivation thereof.

In an example, the image acquisition device 170 may be integrated with the treatment device 180 as a single apparatus (e.g., a MRI device combined with a linear accelerator, also referred to as an "MRI-Linac"). Such an MRI-Linac can be used, for example, to determine a location of a target organ or a target tumor in the patient, so as to direct radiation therapy accurately according to the radiation therapy treatment plan to a predetermined target. For instance, a radiation therapy treatment plan may provide information about a particular radiation dose to be applied to each patient. The radiation therapy treatment plan may also include other radiotherapy information, such as beam angles, dose-histogram-volume information, the number of radiation beams to be used during therapy, the dose per beam, and the like.

The radiotherapy processing computing system 110 may communicate with an external database through a network to send/receive a plurality of various types of data related to image processing and radiotherapy operations. For example, an external database may include machine data (including device constraints) that provides information associated with the treatment device 180, the image acquisition device 170, or other machines relevant to radiotherapy or medical procedures. Machine data information may include radiation beam size, arc placement, beam on and off time duration, machine parameters, segments, multi-leaf collimator (MLC) configuration, gantry speed, MRI pulse sequence, and the like. The external database may be a storage device and may be equipped with appropriate database administration software programs. Further, such databases or data sources may include a plurality of devices or systems located either in a central or a distributed manner.

The radiotherapy processing computing system 110 can collect and obtain data, and communicate with other systems, via a network using one or more communication interfaces, which are communicatively coupled to the processing circuitry 112 and the memory 114. For instance, a communication interface may provide communication connections between the radiotherapy processing computing system 110 and radiotherapy system components (e.g., permitting the exchange of data with external devices). For instance, the communication interface may in some examples have appropriate interfacing circuitry from an output device 146 or an input device 148 to connect to the user interface 142, which may be a hardware keyboard, a keypad, or a touch screen through which a user may input information into the radiotherapy system.

As an example, the output device 146 may include a display device which outputs a representation of the user interface 142 and one or more aspects, visualizations, or representations of the medical images, the treatment plans, and statuses of training, generation, verification, or implementation of such plans. The output device 146 may include one or more display screens that display medical images, interface information, treatment planning parameters (e.g., contours, dosages, beam angles, labels, maps, etc.) treatment plans, a target, localizing a target and/or tracking a target, or any related information to the user. The input device 148 connected to the user interface 142 may be a keyboard, a keypad, a touch screen or any type of device that a user may input information to the radiotherapy system. Alternatively, the output device 146, the input device 148, and features of the user interface 142 may be integrated into a single device such as a smartphone or tablet computer, e.g., Apple iPad®, Lenovo Thinkpad®, Samsung Galaxy®, etc.

Furthermore, any and all components of the radiotherapy system may be implemented as a virtual machine (e.g., via VMWare, Hyper-V, and the like virtualization platforms). For instance, a virtual machine can be software that functions as hardware. Therefore, a virtual machine can include at least one or more virtual processors, one or more virtual memories, and one or more virtual communication interfaces that together function as hardware. For example, the radiotherapy processing computing system 110, the image data sources 150, or like components, may be implemented as a virtual machine or within a cloud-based virtualization environment.

The image processing logic 120 or other software programs may cause the computing system to communicate with the image data sources 150 to read images into memory 114 and the storage device 116, or store images or associated data from the memory 114 or the storage device 116 to and from the image data sources 150. For example, the image data source 150 may be configured to store and provide a plurality of images (e.g., 3D MRI, 4D MRI, 2D MRI slice images, CT images, 2D Fluoroscopy images, X-ray images, raw data from MR scans or CT scans, Digital Imaging and Communications in Medicine (DICOM) metadata, etc.) that the image data source 150 hosts, from image sets in image data 152 obtained from one or more patients via the image acquisition device 170 in model training or generation use cases. The image data source 150 or other databases may also store data to be used by the image processing logic 120 when executing a software program that performs treatment plan operations of creating, modifying, or estimating radiation therapy treatment plans. The radiotherapy processing computing system 110 thus may obtain and/or receive the image data 152 (e.g., 2D MRI slice images, CT images, 2D Fluoroscopy images, X-ray images, 3D MRI images, 4D MRI images, etc.) from the image data source 150, the image acquisition device 170, the treatment device 180 (e.g., a MRI-Linac), or other information systems, in connection with performing radiation treatment or diagnostic operations.

The image acquisition device 170 can be configured to acquire one or more images of the patient's anatomy for a region of interest (e.g., a target organ, a target tumor or both). Each image, typically a 2D image or slice, can include one or more parameters (e.g., a 2D slice thickness, an orientation, and a location, etc.). In an example, the image acquisition device 170 can acquire a 2D slice in any orientation. For example, an orientation of the 2D slice can include a sagittal orientation, a coronal orientation, or an axial orientation. The processing circuitry 112 can adjust one or more parameters, such as the thickness and/or orientation of the 2D slice, to include the target organ and/or target tumor. In an example, 2D slices can be determined from information such as a 3D MRI volume. Such 2D slices can be acquired by the image acquisition device 170 in "near real-time" while a patient is undergoing radiation therapy treatment, for example, when using the treatment device 180 (with "near real-time" meaning acquiring the data in at least milliseconds or less).

The image processing logic 120 in the radiotherapy processing computing system 110 is depicted as implementing an image representation workflow 130, performing aspects of encoding (132), fusion (134), and decoding (136) in connection with generating and using a shared latent representation. The image processing logic 120 is further depicted as implementing an image downstream function workflow 140, to perform one or more downstream tasks as further discussed herein.

The image processing logic 120 may be used when generating a radiation therapy treatment plan, within use or integration of software programs having radiotherapy treatment planning features, such as Monaco®, manufactured by Elekta AB of Stockholm, Sweden. In order to generate the radiation therapy treatment plans, the radiotherapy processing computing system 110 may communicate with the image acquisition device 170 (e.g., a CT device, a MRI device, a PET device, an X-ray device, an ultrasound device, etc.) to capture and access images of the patient and to delineate a target, such as a tumor. In some examples, the delineation of one or more organs at risk (OARs), such as healthy tissue surrounding the tumor or in close proximity to the tumor may be required. Therefore, segmentation of the OAR may be performed when the OAR is close to the target tumor. In addition, if the target tumor is close to the OAR (e.g., prostate in near proximity to the bladder and rectum), then by segmenting the OAR from the tumor, the radiotherapy system may study the dose distribution not only in the target, but also in the OAR.

In order to delineate a target organ or a target tumor from the OAR, medical images, such as MRI images, CT images, PET images, fMRI images, X-ray images, ultrasound images, radiotherapy portal images, SPECT images and the like, of the patient undergoing radiotherapy may be obtained non-invasively by the image acquisition device 170 to reveal the internal structure of a body part. Based on the information from the medical images, a 3D structure and segmentation, labeling, or other identification of the relevant anatomical portion(s) may be obtained, using any combination of automated or human-assisted functions. For example, segmentation and labeling may be deployed in connection with the identification of treatment areas and restricted areas (e.g., areas to avoid treatment), such as with the identification and definition of planning treatment volumes (e.g., to deliver radiotherapy to a tumor or organ of interest) and OAR(s) (e.g., to avoid radiotherapy and radiation exposure in certain organs or tissue areas).

Accordingly, during a treatment planning process, many parameters may be taken into consideration to achieve a balance between efficient treatment of the target tumor (e.g., such that the target tumor receives enough radiation dose for an effective therapy) and low irradiation of the OAR(s) (e.g., the OAR(s) receives as low a radiation dose as possible). Other parameters that may be considered include the location of the target organ and the target tumor, the location of the OAR, and the movement of the target in relation to the OAR. For example, the 3D structure may be obtained by contouring the target or contouring the OAR within each 2D layer or slice of an MRI or CT image and combining the contour of each 2D layer or slice. The contour may be generated manually (e.g., by a physician, dosimetrist, or health care worker using a program such as MONACO™ manufactured by Elekta AB of Stockholm, Sweden) or automatically (e.g., using a program such as the Atlas-based auto-segmentation software, ABAS®, manufactured by Elekta AB of Stockholm, Sweden). Thus, in certain examples, the 2D or 3D structure of a target tumor or an OAR may be generated automatically by the treatment planning software.

After the target tumor and the OAR(s) have been located and delineated, a dosimetrist, physician, or healthcare worker may determine a specific dose of radiation to be applied to the target tumor, as well as any maximum amounts of dose that may be received by the OAR proximate to the tumor (e.g., left and right parotid, optic nerves, eyes, lens, inner ears, spinal cord, brain stem, and the like). After the radiation dose is determined for each anatomical structure (e.g., target tumor, OAR), a process known as inverse planning may be performed to determine one or more treatment plan parameters that would achieve the desired radiation dose distribution. Other aspects of planning activity and including one or more automated or computer-assisted mechanisms (including use of AI and ML techniques) can be used in connection with the image processing features disclosed herein.

The result of the image processing logic 120 and a treatment plan generation workflow (not shown) may produce a radiation therapy treatment plan that may be stored and provided (e.g., as planning data 162 or to data source 160). Some of these treatment parameters may be correlated or coordinated with specific treatment objectives and attempts. For example, tuning one parameter (e.g., weights for different objectives, such as increasing the dose to the target tumor) in an attempt to change the treatment plan may affect at least one other parameter, which in turn may result in the development of a different treatment plan. Thus, the radiotherapy processing computing system 110 may generate a tailored radiation therapy treatment plan that considers these and like parameters in order for the treatment device 180 to provide suitable radiotherapy treatment to the patient.

Figure 2:
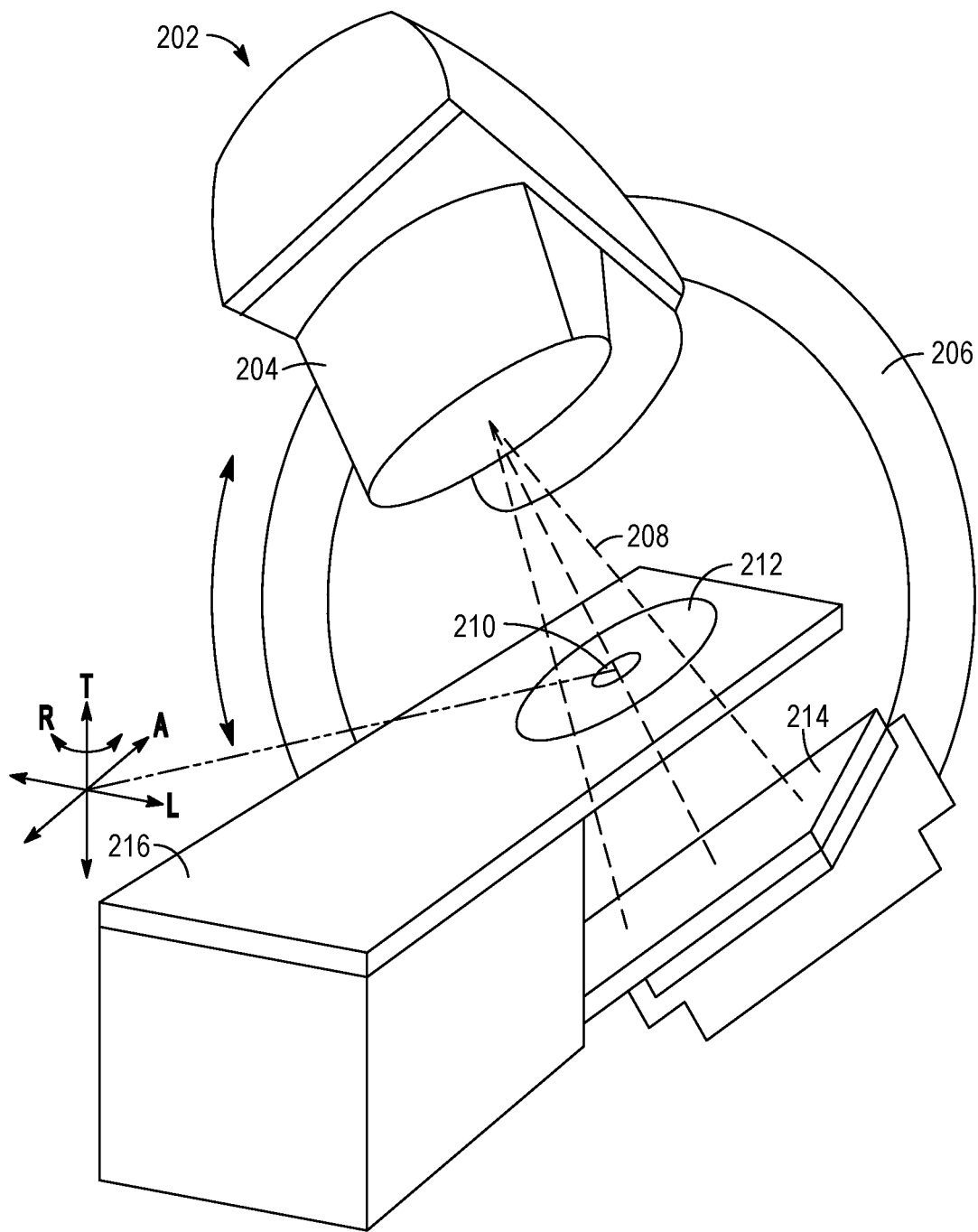
FIG. 2 illustrates an exemplary image-guided radiotherapy device.

FIG. 2 illustrates an exemplary image-guided radiotherapy device 202, that includes include a radiation source, such as an X-ray source or a linear accelerator, a couch 216, an imaging detector 214, and a radiation therapy output 204. The radiation therapy device 202 may be configured to emit a radiation beam 208 to provide therapy to a patient. The radiation therapy output 204 can include one or more attenuators or collimators, such as a multi-leaf collimator (MLC). As will be understood, the radiation therapy output 204 may be provided in connection with aspects of treatment processing logic that implements an image processing workflow, such as with use of segmentation or general representations of multimodal images as discussed herein.

As an example, a patient can be positioned in a region 212, supported by the treatment couch 216 to receive a radiation therapy dose according to a radiation therapy treatment plan (e.g., a treatment plan generated by the radiotherapy system of FIG. 1). The radiation therapy output 204 can be mounted or attached to a gantry 206 or other mechanical support. One or more chassis motors (not shown) may rotate the gantry 206 and the radiation therapy output 204 around couch 216 when the couch 216 is inserted into the treatment area. In an example, gantry 206 may be continuously rotatable around couch 216 when the couch 216 is inserted into the treatment area. In another example, gantry 206 may rotate to a predetermined position when the couch 216 is inserted into the treatment area. For example, the gantry 206 can be configured to rotate the therapy output 204 around an axis ("A"). Both the couch 216 and the radiation therapy output 204 can be independently moveable to other positions around the patient, such as moveable in transverse direction ("T"), moveable in a lateral direction ("L"), or as rotation about one or more other axes, such as rotation about a transverse axis (indicated as "R"). A controller communicatively connected to one or more actuators (not shown) may control the couch 216 movements or rotations in order to properly position the patient in or out of the radiation beam 208 according to a radiation therapy treatment plan. As both the couch 216 and the gantry 206 are independently moveable from one another in multiple degrees of freedom, which allows the patient to be positioned such that the radiation beam 208 precisely can target the tumor.

The coordinate system (including axes A, T, and L) shown in FIG. 2 can have an origin located at an isocenter 210. The isocenter can be defined as a location where the central axis of the radiation therapy beam 208 intersects the origin of a coordinate axis, such as to deliver a prescribed radiation dose to a location on or within a patient. Alternatively, the isocenter 210 can be defined as a location where the central axis of the radiation therapy beam 208 intersects the patient for various rotational positions of the radiation therapy output 204 as positioned by the gantry 206 around the axis A.

Gantry 206 may also have an attached imaging detector 214. The imaging detector 214 is preferably located opposite to the radiation source (output 204), and in an example, the imaging detector 214 can be located within a field of the therapy beam 208.

The imaging detector 214 can be mounted on the gantry 206 preferably opposite the radiation therapy output 204, such as to maintain alignment with the therapy beam 208. The imaging detector 214 rotating about the rotational axis as the gantry 206 rotates. In an example, the imaging detector 214 can be a flat panel detector (e.g., a direct detector or a scintillator detector). In this manner, the imaging detector 214 can be used to monitor the therapy beam 208 or the imaging detector 214 can be used for imaging the patient's anatomy, such as portal imaging. The control circuitry of radiation therapy device 202 may be integrated within the radiotherapy system or remote from it.

In an illustrative example, one or more of the couch 216, the therapy output 204, or the gantry 206 can be automatically positioned, and the therapy output 204 can establish the therapy beam 208 according to a specified dose for a particular therapy delivery instance. A sequence of therapy deliveries can be specified according to a radiation therapy treatment plan, such as using one or more different orientations or locations of the gantry 206, couch 216, or therapy output 204. The therapy deliveries can occur sequentially, but can intersect in a desired therapy locus on or within the patient, such as at the isocenter 210. A prescribed cumulative dose of radiation therapy can thereby be delivered to the therapy locus while damage to tissue nearby the therapy locus can be reduced or avoided.

Thus, FIG. 2 specifically illustrates an example of a radiation therapy device 202 operable to provide radiotherapy treatment to a patient, with a configuration where a radiation therapy output can be rotated around a central axis (e.g., an axis "A"). Other radiation therapy output configurations can be used. For example, a radiation therapy output can be mounted to a robotic arm or manipulator having multiple degrees of freedom. In yet another example, the therapy output can be fixed, such as located in a region laterally separated from the patient, and a platform supporting the patient can be used to align a radiation therapy isocenter with a specified target locus within the patient. In another example, a radiation therapy device can be a combination of a linear accelerator and an image acquisition device. In some examples, the image acquisition device may be a MRI, an X-ray, a CT, a CBCT, a spiral CT, a PET, a SPECT, an optical tomography, a fluorescence imaging, ultrasound imaging, or radiotherapy portal imaging device, etc., as would be recognized by one of ordinary skill in the art.

Image analysis is essential to locate the conditions (e.g., a brain tumor) for treatment planning and evaluation. Unlike surgery—during which tumors can be seen directly by surgeons—radiation therapy relies heavily on the detection of tumors through non-invasive imaging methods. Inaccurate radiation delivery does not only fail to kill the tumor, but also mistreats healthy tissue. It is, therefore, of utmost importance to segment the tumor precisely.

Image analysis is a general term describing the extraction of useful information from images. It includes feature detection, image description, segmentation, recognition, classification and more. Objects are often detected based on their physical characteristics. Discontinuities in image brightness due to difference in depth, surface orientation and structure provide distinctive features. Shape, color and size are some common features that are used to describe objects in the image. In segmentation, thresholding is a common low-level technique that detects objects in accordance to the pixels intensities. Further, there are methods that consider spatial information such Normalized Cuts, Split-and-Merge, and Mean-Shift algorithm. Feature selection for these algorithms is therefore paramount.

The following techniques discuss the use of specific encoding and fusion techniques for use with image analysis and image data processing, for purposes such as segmentation, classification, and the like. Accordingly, the use of a shared latent representation may provide significant benefits for a number of image processing functions, and the resulting radiotherapy treatment protocol or workflow.

Figure 3:
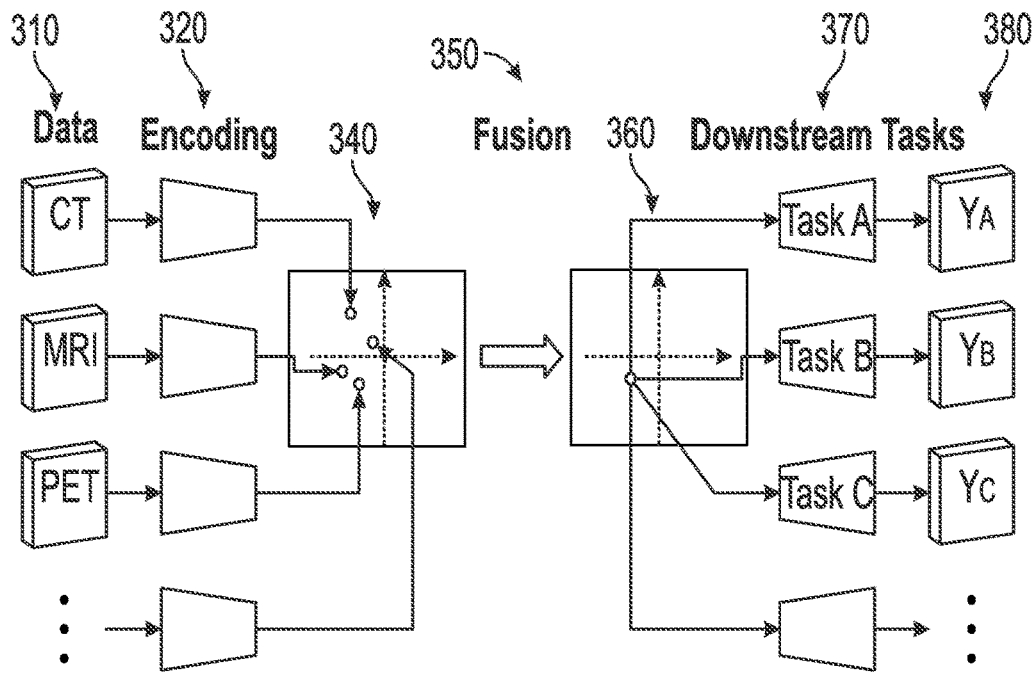
FIG. 3 illustrates an exemplary encoding and fusion technique using a shared latent representation for use in radiotherapy imaging processing tasks.

FIG. 3 illustrates an exemplary encoding and fusion technique using a shared latent representation for use in radiotherapy imaging processing tasks. Specifically, the technique of FIG. 3 involves methods from representation learning in order to find a common basis for representation of medical images. This common representation can then be used as input to the function $f_\theta$ above.

In an example, the image processing approach depicted in FIG. 3, can be subdivided into three sequential processing operations:

1) Encoding. In the encoding operation (320), each input datum (310) is mapped to a shared latent representation.

2) Fusion. In the fusion operation (350), all the resulting data points are reduced to a single data point (340).

3) Downstream tasks. Each of the one or several downstream tasks (370) takes the unified representation as input (360) and produces corresponding output (380).

The output of at least one of the downstream tasks is used in the function $f_\theta$ to guide the learning. When important, a distinction is made between training tasks, which are used in the learning, and auxiliary tasks, which are not. Examples of downstream tasks include segmentation, denoising, image synthesis, classification, regression, or reconstruction.

When there are only small amounts of data available for a downstream task, the presently disclosed method can help improve the performance by leveraging information from the unified representation that has been learned on other tasks. In other words, the method can be used for semi-supervised learning. As a result, it may be necessary to enforce some type of regularity (e.g. smoothness) of the latent representation during encoding, which can be done using, for instance, a variational autoencoder. It may also be preferable to have a latent representation which has the same spatial coordinates as the images so that the variables can be interpreted locally. This technique is introduced using Gaussian random fields in various examples below.

The encoding step and the downstream tasks could be either modality specific or not. If they are not, then the method would—in theory—work also with a previously unseen type of input modality, at least if it is sufficiently similar to those used in the training. Thus, one example implementation of the encoding step and the downstream tasks may be provided with use of a neural network, but other implementations may be used.

The main requirement on the fusion step is that it can take a variable number of input points and reduce them to a single point. Simple functions capable of this include the mean and the maximum, but the following examples describe a more general approach whereby the fusion can be learned.

Limited approaches have been attempted to perform multimodal image synthesis. For instance, Chartsias et al., "Multimodal MR Synthesis via Modality-Invariant Latent Representation", describe a method for image synthesis based on a deep fully convolutional network model. In this method, synthesis refers to taking a number of images, showing the same organs in different modalities, as input, and outputting synthetic images of that same anatomy in one or more new modalities. In the Chartsias approach, independent encoders are used for each input modality, and a fusion step, is applied that utilizes a pixelwise maximum.

Simply embedding inputs into the same representation space, however, does not ensure that they share a meaningful latent representation. The embeddings, if not encouraged to do so, have no reason to use the latent space in a comparable way. If this is the case, then decoding one latent representation is distinct from decoding the other, and moreover, fusion becomes difficult, as operations such as taking the mean are no longer meaningful. As a result, to enforce a desirable structure in the latent space representation and good performance on the reconstruction task, the Chartsias approach uses a specific three-component cost function, using the following constraints:

1. Each modality's individual latent representation should produce all outputs as accurately as possible. The corresponding cost term is a pixelwise L1-loss averaged over all input modalities, individually, and all outputs.

2. The latent representations from all input modalities should be close in the Euclidean sense. The corresponding cost term is a pixelwise variance averaged over all pixels and channels in the latent representations (i.e. before fusion).

3. The fused latent representation should produce all outputs as accurately as possible. The corresponding cost term is a pixelwise L1 reconstruction loss.

However, the second component does not enforce any structure on the latent representation, and hence this model is not a generative model, nor is the latent representation necessarily stable with respect to the input. As a result, the latent representation produced by the Chartsias approach would not be stable if used as input to some other learning algorithm.

The presently disclosed technique enables use of a more widely applicable fusion operation than the Chartsias technique or other conventional approaches. Specifically, the disclosed technique enables satisfaction of the following requirements:

1) A valid fusion operation a needs to map any number of latent representations $z_i$ into a single one, $\hat{z}$.

2) The fusion operator should conserve any structure required from the latent variables (e.g. Gaussian-ness).

This criteria is fulfilled (up to a scale factor) by the dot product or, more generally, an inner product $(\bullet, \bullet)$ defined on vector spaces with variable dimension n.

Figure 4:
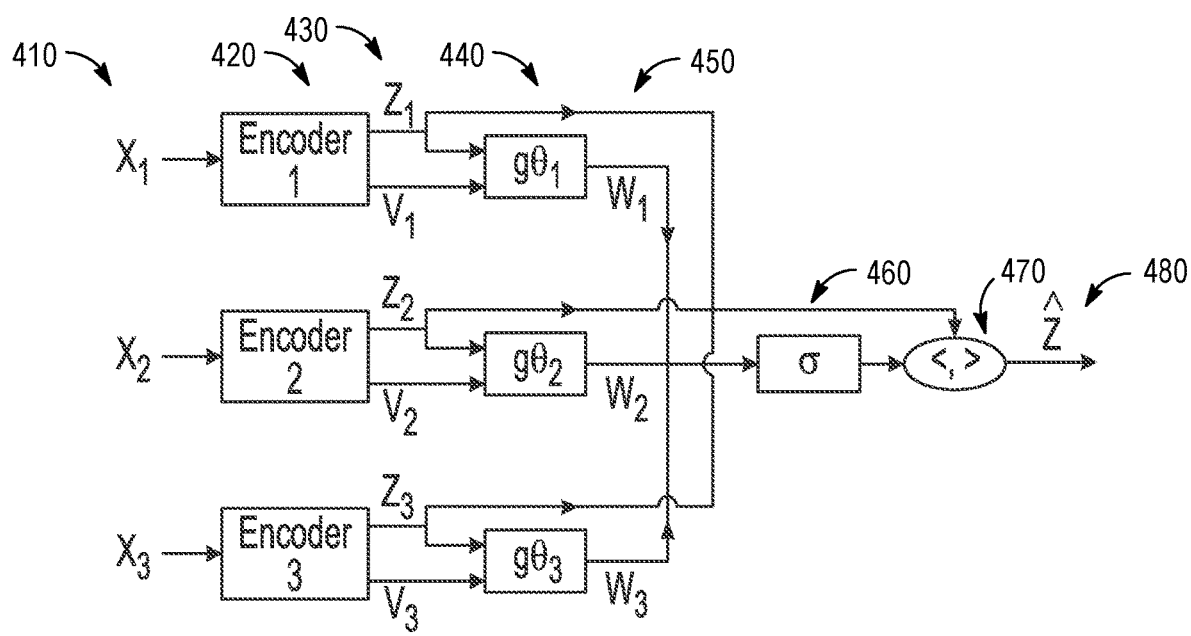
FIG. 4 illustrates an exemplary schematic for learning a general fusion operation for use in image processing techniques.

FIG. 4 illustrates an exemplary schematic for learning a general fusion operation for use in image processing techniques, such as the radiotherapy imaging processing tasks discussed above. With the depicted techniques, each encoder (420) for a given input (410) outputs (430) a confidence value $v_i$ in addition to the latent space representation $z_i$. Both of these values are used as inputs to a, possibly learnable, function $g_{\theta_i}$ (440) which outputs a confidence weighting $w_i = g_{\theta_i}(z_i, v_i)$ (450). In another example, it the fusion operation may be defined as $\hat{z} = (w, z)$. It is reasonable to require that the confidence weights are nonnegative and sum to unity, otherwise there may be ambiguity in the scale of the latent representation. This can be achieved pointwise (e.g., in an image) by squashing the confidence weights using the soft-max (normalized exponential) function, according to:

$$\sigma(w_i) = \frac{\exp(w_i)}{\sum_{j=1}^{n} \exp(w_j)}$$

The fusion operation $\hat{z}$ (480) can thus be represented as $\hat{z} = (\sigma(w), z)$ (as indicated in 460, 470). Accordingly, this provides benefits over conventional approaches.

First, suppose $g(z, v) = 0$ (or any other constant) identically, then $\sigma(w_i) = 1/n$. In other words, this results in mean fusion. Second, suppose that the soft-max is used to take $w_i = 1$ if $z_i = \max(z_1, \ldots, z_n)$ and 0 otherwise. Then, the result is provided in max fusion. Third, the simple choice $g(z, v) = v$ gives a soft-max weighting of the latent space representations.

More generally, the function(s) $g_{\theta_i}$ (440) could be learnable and parameterized as, for instance, convolutional neural network(s). Some types of input data are more likely to be informative of certain types of tissue or for certain channels in the latent representation. The learned weighting acts as an attention mechanism that makes it possible to focus on the most informative data sources and the most informative regions according to the training tasks. Incidentally, such attention mechanisms have been very successful in recent years.

In further examples, attention mechanisms may be adapted to improve the operation of the presently disclosed techniques. In the context of neural networks, attention refers to a mechanism of selectively focusing on the most informative parts of the input. For an example, attention mechanisms have proven very successful in particular for natural language processing and automatic image captioning. In such settings, there is a variable number of inputs (e.g., words) but they have an ordering that makes it appropriate to use e.g. a recurrent neural network or a temporal convolution.

With the present image processing techniques, there are a variable number of medical images as input. Further, there typically isn't any natural ordering among medical images (except for limited exceptions such as longitudinal scans). The presently disclosed fusion mechanism could incorporate learned attention models $g_{\theta_i}$ (possibly different for each input modality) that outputs confidence weights $w_i = g_{\theta_i}(z_i, v_i)$. Further, these confidence weights can be generated independently for each input modality. In a later step, it might be desirable to recalibrate the individual confidence weights using e.g. a soft-max function.

In an example, the latent representations $z_i$ estimated from each of the (arbitrary number of) modalities i separately must all have the same dimensions. If the fusion uses an inner product, described above, then the two variables that enter the inner product need to have the same dimensions (typically one of them being the latent representation estimated from the that modality and the other being (a function of) the confidence weights). In particular, the guide variables $v_i$ need not have any particular dimensions and can even be different for different modalities.

The table below (TABLE 1) illustrates an example of possible dimensions in a particular model that only fuses information from two input modalities.

TABLE 1

| DESCRIPTION | SYMBOL | HEIGHT | WIDTH | DEPTH | CHANNELS |
|---|---|---|---|---|---|
| INPUT (CT) | $x_1$ | 512 | 512 | 512 | 1 |
| LATENT REP. | $z_1$ | 256 | 256 | 128 | 16 |
| GUIDE | $v_1$ | 256 | 256 | 128 | 16 |
| CONFIDENCE | $w_1$ | 256 | 256 | 128 | 16 |
| INPUT (MR) | $x_2$ | 256 | 256 | 128 | 1 |
| LATENT REP. | $z_2$ | 256 | 256 | 128 | 16 |
| GUIDE | $v_2$ | 1 | 1 | 1 | 1 |
| CONFIDENCE | $w_2$ | 256 | 256 | 128 | 16 |

In an example, the first attention model could be a fully convolutional neural network, having, for instance, a U-net architecture. The second attention model could be a convex combination of two models, such as $$w_2 = g_{\theta_2}(z_2, v_2) = \frac{f_a(v_2) + \exp(-v_2)f_b(z_2)}{1 + \exp(-v_2)},$$

where, further, $f_a$ may be the pixelwise maximum and $f_b$ may be a Gaussian process regression model. To arrive at a single estimate $\hat{z}$ of the latent space representation, the arguably simplest way is by forming the weighted sum $\hat{z} = w_1 z_1 + w_2 z_2$.

In a further example, intuition on the image or imaging procedure may be employed to enhance the use of an attention model in medical imaging processing. Specifically, different input modalities provide information on different things. Suppose one of the channels in the latent representation corresponds to the density in different parts of the image. Then, Computed tomography (CT) would be highly informative everywhere, so if CT imaging is present almost all the weight can be placed on the latent representation estimated from that. An example of a more complicated scenario is if CT imaging is not present but two types of MR imaging are used: a standard T1-weighted MRI and an Ultrashort Echo Time (UTE) MRI. The T1-weighted MRI has very high soft tissue contrast, so it would be informative about the density in the soft tissue. On the other hand, T1-weighted MRI cannot distinguish between cortical bone (the densest tissue) and air (basically zero density). In contrast, UTE MRI can image cortical bone reasonably well but has poorer soft tissue contrast. In this scenario, more weight can be given to the T1 image in soft tissue areas and, conversely, more weight to the UTE MRI in bony areas. Recall, however, that if CT imaging is available then the information from the MR scans can be disregarded. The attention mechanism is a way of learning how to best perform this tradeoff between the different sources of information.

In further examples, variational auto-encoders may be utilized to explore or sample from the latent distribution. Variational auto-encoders can be used to add a structure to the latent representation, however the latent variables in standard auto-encoder does not have a spatial representation (it is simply a vector in Rn), and hence the latent representation cannot be directly interpreted as an image. As a result, spatial latent variables may be added to the presently disclosed fusion techniques. By combining these methods, a method is produced that has all the properties from a latent representation.

As an overview of auto-encoders and variational auto-encoders, consider that auto-encoders, work by training two networks simultaneously. The encoder E takes data as input and maps it to a latent variable z, while the decoder D takes the latent variable z and reconstructs the input from it. The networks are trained by minimizing the reconstruction loss, typically taken to be the expected mean squared error:

$$L = \mathbb{E}[\|D(E(X)) - X\|_2^2]$$

Once the network has been trained, new samples can be generated by taking randomly sampled z and computing D(z). However, to get proper samples from X, z~E(X) is needed, but in general the distribution of the random variable E(X) is not known. Due to this problem, classical auto-encoders cannot be used for generative modelling.

One way to solve this issue is to enforce that the latent variable has a particular distribution. For example, assume E(X) has a multivariate normal distribution N ($\mu_1$, $\Sigma_1$).

Instead of enforcement, a technique can reverse the Kullback-Leibler distance from E(X) to N ($\mu_1$, $\Sigma_1$) as follows:

$$L = \mathbb{E}[\|D(E(X)) - X\|_2^2] + \lambda KL(\mathcal{N}(\mu_1, \Sigma_1) \| E(X))$$

However, this is also hard to compute because for empirical distributions E(X) is singular with respect to N(0, I) and the Kullback-Leibler distance is thus always infinite. Some minor tricks can deal with this, but this causes the optimization to be become unstable. To solve this, prior approaches have proposed the variational auto-encoder (VAE). This makes the generator probabilistic, which allows a stable computation of the Kullback-Leibler distance. In particular, prior approaches have proposed that the encoder could return a normal distribution, in which case it is sufficient if the output has two parts, $\mu$ and $\Sigma$, representing the mean and covariance.

By parameterizing $\mu$, $\Sigma$, and D by with neural networks, this optimization problem can be solved using standard stochastic gradient descent methods, and once trained X can be sampled by taking z~N(0, I) and computing D(z). Accordingly, in prior literature, the latent space structure is almost always chosen to be one with diagonal covariances, which means that it is essentially a feature vector with independent elements. On the contrary, an image may indicate strong spatial correlations: by knowing the local neighborhood of a pixel, many things can be inferred about the likely values in that pixel.

In a further application of the present techniques, a variational auto-encoder may be tailored for images to exhibit spatial correlations in the latent space. By enforcing such structure, improvements may be introduced to the performance of a conventional VAE, both for general image processing and for any particular application of medical imaging processing. In the following techniques, such structure can be imposed and, notably, can be performed in a computationally efficient manner.

In an example, various latent representation models may utilize output from variational auto-encoders in connection with the presently disclosed image processing techniques. In a particular example, Gaussian random fields may be used to combine the information bottleneck of classical VAE with the spatial representation of random fields.

In an example, let $\Omega \subseteq Rd$. A Gaussian random field $f$ is a random variable $\Omega \to R$ such that for any $n \in Z+$, (x1, x2, . . . , xn)$\in$(Rd)n, the random vector ($f$ (x1), $f$ (x2), . . . , $f$ (xn)) is a multivariate Gaussian random variable with mean $\mu$(x1, x2, . . . , xn) and co-variance matrix $\Sigma$(x1, x2, . . . , xn). Here, the interest is in covariance matrices that reflect spatial correlation, in other words, covariance matrices that are not diagonal.

A range of computationally efficient methods of expressing such structure have been proposed with existing techniques, such as spectral representations (using the discrete Fourier transform), covariance tapering (setting small values in the covariance to zero), low rank approximations (exact computations on a model with reduced rank) and Gaussian Markov Random Fields (sparse precision matrix).

Here, the assumption is that the covariance Cov ($f$ (x1), $f$ (x2)) is translation invariant, i.e. a function of only the difference x1−x2. In this setting, the covariance is of the form $\Sigma$(x1, x2)=K(x1−x2) where K is called the (covariance)) kernel. A typical form of K is the Gaussian K($x_1 - x_2$)=exp($-\|x\|^2/2\sigma^2$)) where $\sigma \in R$ is the standard deviation (width) of the kernel.

Starting from the exposition of a typical VAE, it is straightforward to combine it with Gaussian random fields. In particular, the reference standard deviation is selected to that of some reference Gaussian random field (typically with a Gaussian kernel). This implies that the action of the covariance is simply a convolution $\Sigma_{1y}=K*y$ where * denotes convolution, the mean $\mu_1$ can still be set to zero.

On the other hand, for the outputs of the neural network $\mu(x)$, $\Sigma(x)$: $\mu(x)$ may be performed with a classical auto-encoder to allow the encoder to freely learn; whereas for $\Sigma(x)$, allowing the encoder to learn the whole covariance matrix may be too costly. Inspired by the classical choice of letting $\Sigma(x)$ be a diagonal matrix, a similar approach may be used. In particular, this may be represented by:

$$\Sigma 2y = K*(\sigma 2 \circ y)$$

where ° is the Hadamard (pointwise) product and only $\sigma$ is learned. With this choice, the Kullback-Leibler divergence is simply $$KL(\mathcal{N}(\mu_2,\Sigma_2)\|\mathcal{N}(\mu_1,\Sigma_1)) = \tfrac{1}{2}[-\int_\Omega \log \sigma^2(s)ds - \int_\Omega ds + \int_\Omega \sigma^2(s)ds + \int_\Omega (\Sigma_1^{-1/2}\mu_2(s))^2 ds]$$

Hence to compute the loss, $\Sigma_1^{-1/2}$ is computed; however, given that if K is a Gaussian kernel, the Fourier convolution theorem states $$K*y = \mathcal{F}^{-1}(FK \circ Fy)$$

With the result that:

$$(K*)^{-1/2}y = \mathcal{F}^{-1}((FK)^{-1/2} \circ Fy$$

as can be verified by straightforward computation:

$$(K*)^{-1/2}(K*)^{-1/2}K*y = \mathcal{F}^{-1}\left(\begin{matrix}(\mathcal{F}K)^{-1/2} \circ \mathcal{F}\mathcal{F}^{-1} \\ ((\mathcal{F}K)^{-1/2} \circ \mathcal{F}\mathcal{F}^{-1}(\mathcal{F}K \circ \mathcal{F}y))\end{matrix}\right)$$
$$= \mathcal{F}^{-1}((\mathcal{F}K)^{-1/2} \circ (\mathcal{F}K)^{-1/2} \circ \mathcal{F}K\mathcal{F}y)$$
$$= \mathcal{F}^{-1}(\mathcal{F}y)$$
$$= y$$

Given all of this, the (reverse) Kullback-Leibler divergence can be easily computed, and hence using this type of prior VAE computation is possible.

In an example, the fusion operator α is a function that takes the output from the encoders, and "fuses" them, creating the fused latent representation. In the specific language of variational auto-encoders with Gaussian latent variables, every encoder Ei outputs a pair Ei(xi)=($\mu$i, $\Sigma$i) where $\mu$i is the mean, containing the information we're interested in, and $\Sigma$i is the covariance, indicating the inaccuracy of the result. The fusion is thus a mapping taking any number of such pairs and returning a pair ($\mu$, $\Sigma$).

In an example, a requirement of the fusion operator is that it preserves whatever structure in the latent variables. For example, if Gaussian Random Fields are used, then the fusion should also be a Gaussian random field. Further, structural requirements may be used on the latent variable (for clarity, an example is given with only two encoders, but the principle is the same regardless of the number of encoders/modalities).

One structure requirement is that if a modality is wholly uninformative (e.g., lim $\Sigma$->∞), then it should not change the latent variable. Without writing out the limits, this means:

$$\alpha((\mu 1, \Sigma 1),(\mu 2, \infty)) = (\mu 1, \Sigma 1)$$

In practice, this also means that nothing is lost by adding uninformative modalities. On the other hand, if the modality has perfect information (lim $\Sigma$->0), then it should exactly determine the value of the latent variable:

$$\alpha((\mu 1, \Sigma 1),(\mu 2, 0)) = (\mu 2, 0)$$

For values "in between", there may be some interpolating effect, with the expectation that the fusion respects the fact that adding more information should always be helpful, or at worst do nothing.

Finally, the latent representation may be vector valued, so the above examples should be interpreted, for instance, pointwise. Accordingly, there may be many applicable functions satisfying the above requirements, with the main difference being how they interpolate in between the extreme cases.

Figure 5:
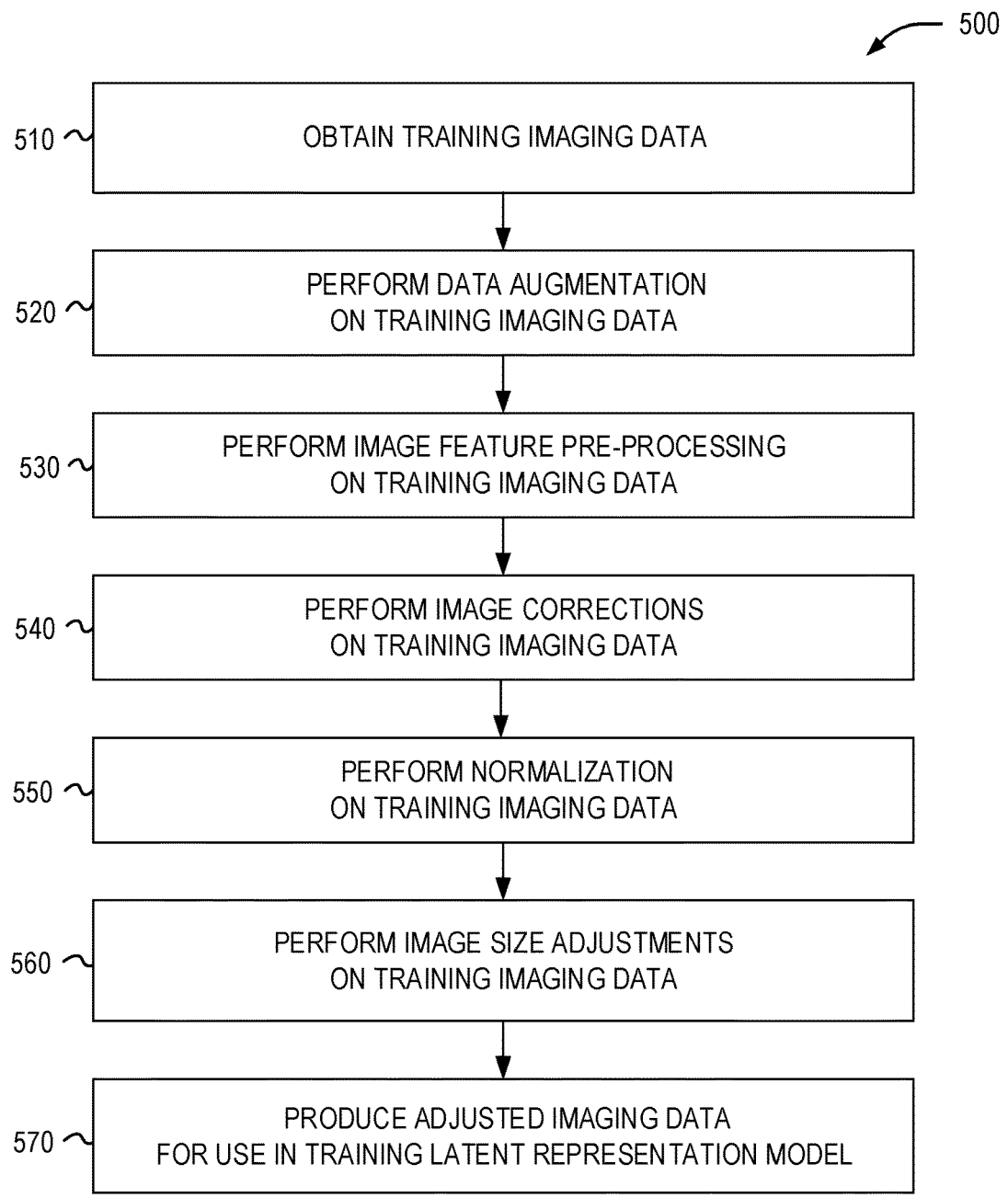
FIG. 5 illustrates a flowchart of exemplary operations for pre-processing medical imaging data used in connection with training of a modality-agnostic imaging processing model.

As a further illustration of the end-to-end processing occurring as part of training a modality-agnostic imaging processing model (e.g., for use with the radiotherapy imaging processing tasks discussed above), the following figures illustrate specific example implementations of imaging data pre-processing (FIG. 5) and configurations of an encoder model (FIG. 6) implemented in various forms of neural networks (FIGS. 7 to 10). For instance, FIG. 5 illustrates a flowchart 500 of exemplary operations for pre-processing medical imaging data used in connection with training of a modality-agnostic imaging processing model. However, similar imaging processing techniques may also be implemented as part of operating, using, or testing the imaging processing model or other aspects of image processing workflows.

First, training data for encoding and processing is obtained and pre-processed (operation 510). For instance, such data may comprise images from different medical institutions with different clinical protocols and scanners. In the examples of MRI images, such data may include T1-weighted, post-contrast T1-weighted (T1c), T2-weighted and Fluid Attenuated Inversion Recovery (FLAIR) volumes. As a specific example, for training of imaging processing operations from brain tumor imaging, such volumes may include the whole brain MRI scans of patients whom had been pathologically confirmed with glioblastoma (HGG) and lower grade glioma (LGG). The data may be further pre-processed, for example, using image registration or removal of anatomical features (e.g., to remove skulls to only leave soft tissues). removal procedures.

The operations of the flowchart 500 continue with data augmentation (operation 520). Data augmentation may be performed to increase the variety of data such that the classifier learned can be more generalized and lead to less overfitting. Data augmentation may include, for instance, image rotation, left-right flipping, or elastic transformation.

The operations of the flowchart 500 also continue with image feature pre-processing (operation 530). The aim of preprocessing is to maximize the spatial and intensity similarity of same tissues within volumes, as well as between patients. Same tissue types could therefore be acknowledged as same substances given the inhomogeneity effects resulted from acquisition difference during scans. In some examples, the preprocessing may focus on aspects such as background voxel removal, cropping, bias field correction and normalization.

The operations of the flowchart 500 also continue with image corrections (operation 540) such as with Bias Field Correction. Intensity inhomogeneity in the MR scan may be corrected, for instance, through bias field correction. As an example, such correction may be based on a nonparametric nonuniform intensity normalization (N3) algorithm, which derives a non-parametric model that describes tissue intensities directly from the data iteratively. It requires little prior knowledge of the data.

The operations of the flowchart 500 also continue with normalization (operation 550). For instance, histogram equalization may be performed to redistribute the intensity as evenly as possible. The contrast level of different tissue types in the input MR brain data may be increased, particularly between normal tissues and tumor tissue in order to improve the segmentation performance. After the uniform redistribution, the intensity levels may be normalized, for instance, from 0 to 1.

The operations of the flowchart 500 continue with image size adjustments, such as with cropping and rescaling (operation 560). This may include removal of background voxels in order to remove redundant information from the volumes. Without non-informative voxels, the training and validating process can be sped up. This may be performed by finding the minimal and maximal positions of non-zero values in all dimensions in volumes. The input was also rescaled in order to fit the neural network. Finally, the operations of the flowchart 500 conclude by producing the adjusted imaging data (operation 670) for use in training the latent representation model.

Figure 6:
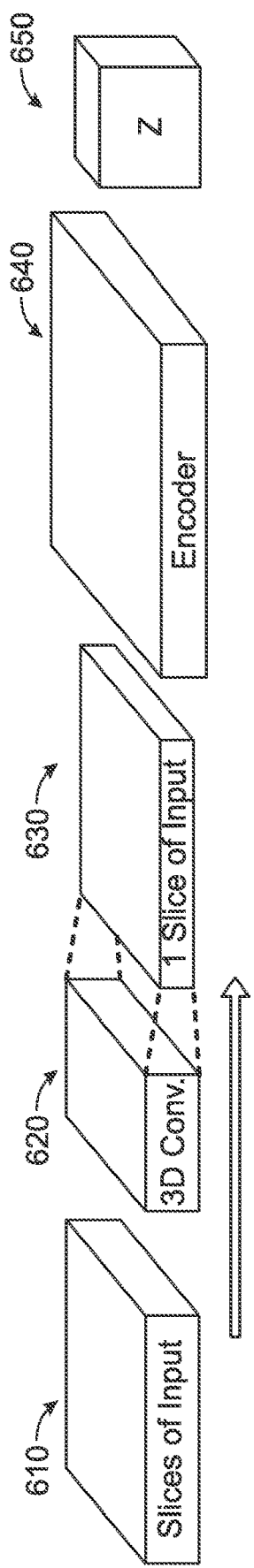
FIG. 6 illustrates a data flow diagram of an exemplary encoding process involving an encoder model, used in connection with training and use of a modality-agnostic imaging processing model.

FIG. 6 illustrates a data flow diagram of an exemplary encoding process performed with an encoder model, used in connection with training and use of a modality-agnostic imaging processing model. As indicated above (e.g., in FIG. 4), multiple encoders may be used as part of a single fusion model. Thus, the encoder model may be specific to a particular imaging modality (e.g., of a certain imaging modality type and operational mode, such as MRI T1); however, the encoder model in other examples may be generic to multiple modality types, modes, or characteristics. As shown, slices of inputs (610) are fed into a 3D convolutional layer (620) before the encoder for each model. Each slide (630) is then produced into the encoder (640), which then produces an output z (650).

Figure 7:
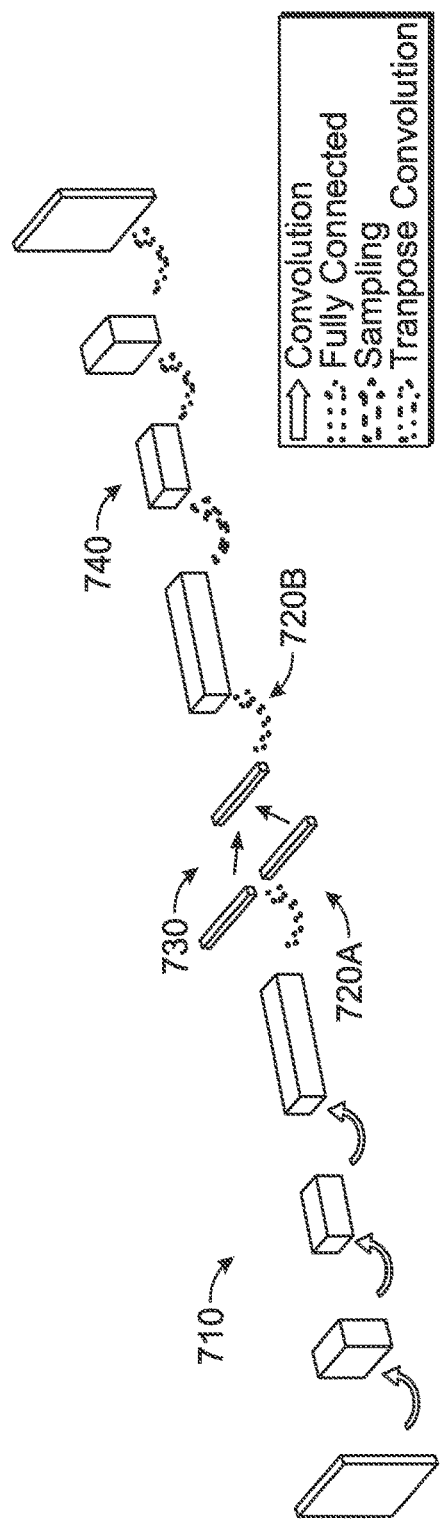
FIG. 7 illustrates a data flow diagram of a variational autoencoder, employed in an exemplary encoding process for generating a latent representation of an imaging input.
Figure 8:
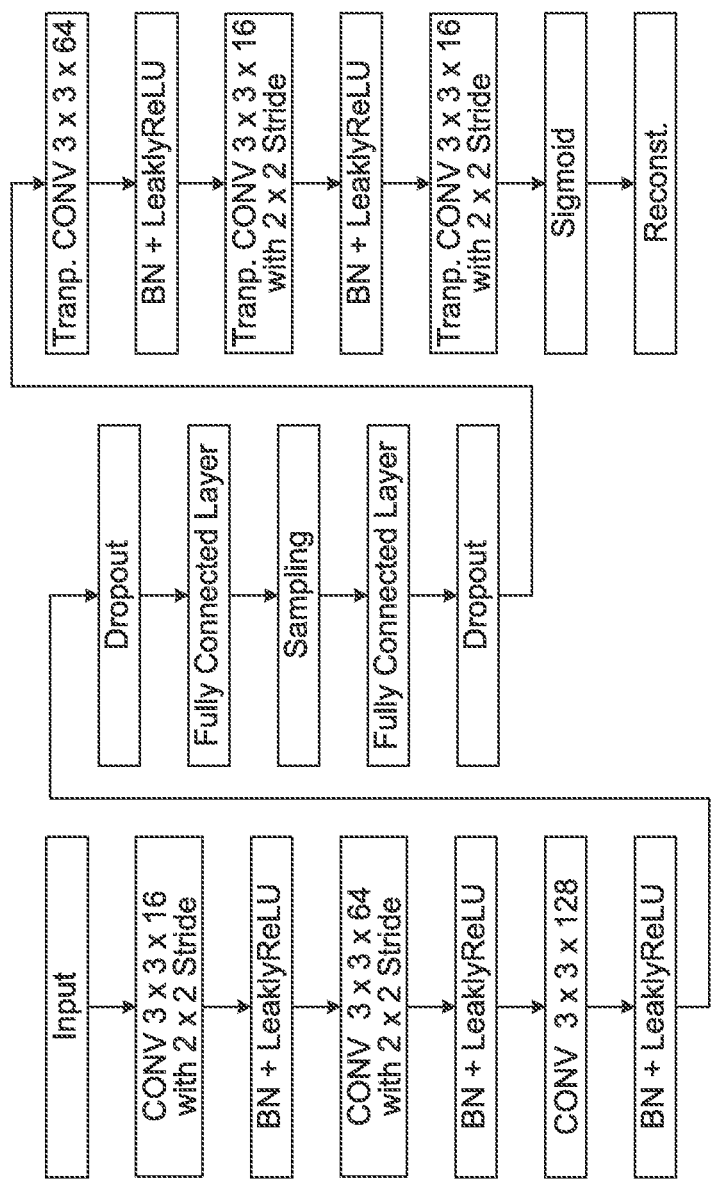
FIG. 8 illustrates data processing operations performed by a neural network of a variational autoencoder, employed in an exemplary encoding process for generating a latent representation of an imaging input.
Figure 9:
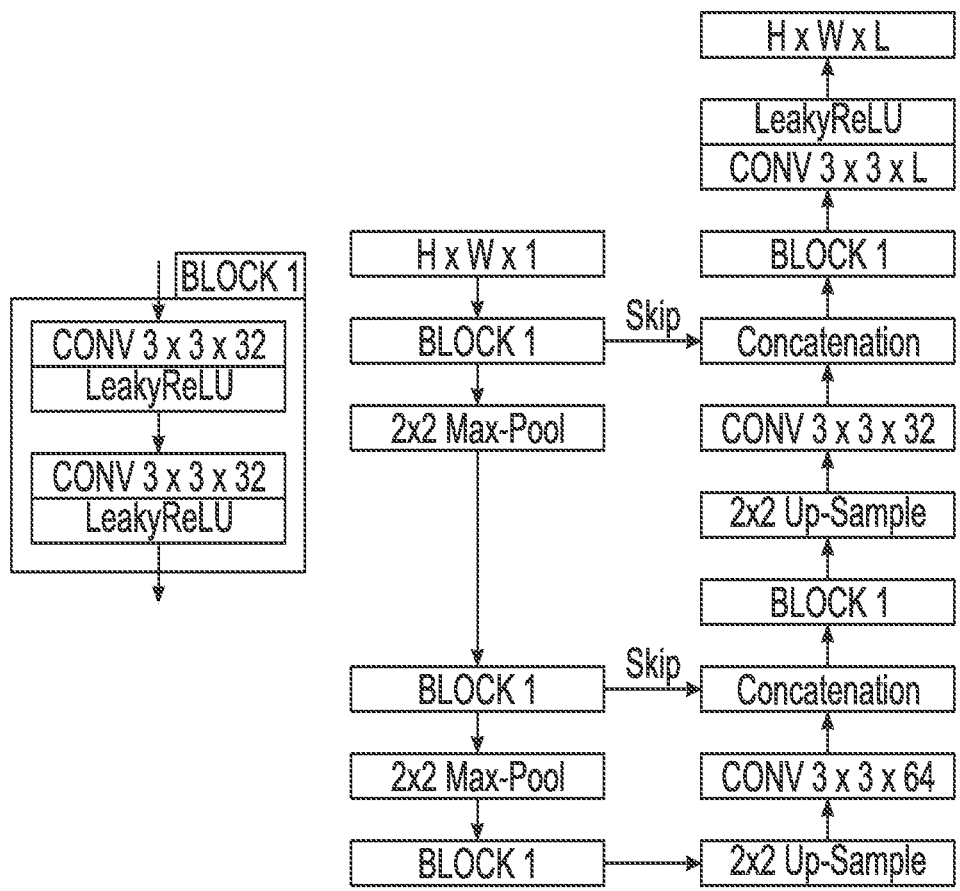
FIGS. 9 and 10 illustrate data processing operations performed by neural networks of a respective encoder and decoder, employed in an exemplary encoding process for generating and using a latent representation of an imaging input.
Figure 10:
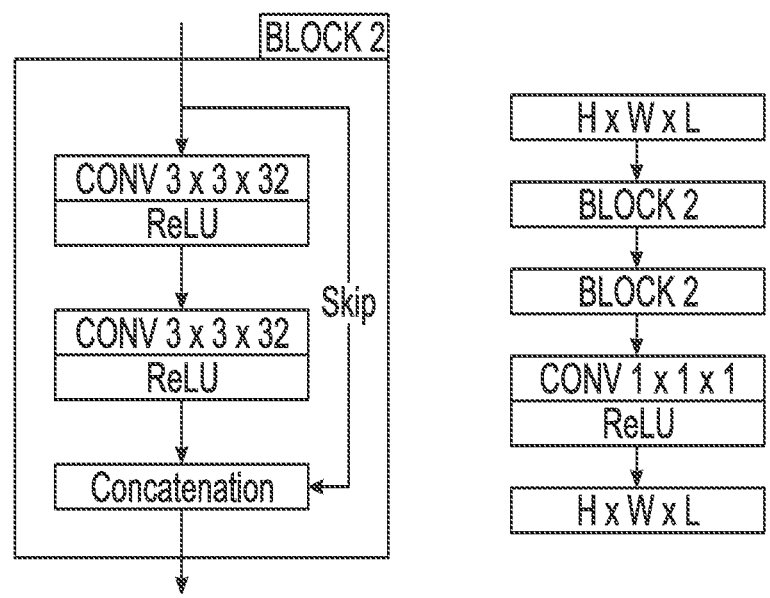

In an example, the implementation of the encoder model as part of the presently described latent representation fusion process may involve the use of a deep neural network to operate an autoencoder. In a first example, this neural network is implemented through a variational encoder neural network. In a second example, this neural network is implemented through encoder and decoder neural networks, where an encoder converts input data into latent representation and decoder reconstruct the input data with the encoded latent representations. This first approach for variational autoencoding is depicted in FIGS. 7 and 8, whereas this second approach for encoding and decoding is depicted in FIGS. 9 and 10. Each of these approaches in the following examples may be usable to learn the latent representation, but with different latent space dimensions and network architecture.

FIG. 7 illustrates a data flow diagram of a variational autoencoder, employed in an exemplary encoding process for generating a latent representation of an imaging input. The variational autoencoder is composed of an encoder and a decoder. As shown, the variational autoencoder includes three blocks of convolutional layers in both the encoder (710) and decoder (740) portions of the network. Input data is encoded to a latent vector in the latent space. It is then decoded to reconstruct the input data. As an example, a latent vector is sampled with the mean and standard deviation by reparameterization. As shown, the variational autoencoder involves use of convolution operations (710), and fully connected operations (720A, 720B) that involve sampling (730). The decoding portion of the variational autoencoder further involves transpose convolution operations (740) that can recreate the original data input. FIG. 8 more specifically illustrates these and more detailed data processing operations performed by a neural network of a variational autoencoder, in connection with input convolution processing operations 810, result generation operations 820, and output transpose convolution processing operations 830 (e.g., producing a value useful for reconstruction).

FIGS. 9 and 10 illustrate data processing operations performed by neural networks of a respective encoder and decoder, employed in an exemplary encoding process for generating and using a latent representation of an imaging input. The encoder, shown in FIG. 9, includes a configuration that is similar to the U-Net but shallower, with only two downsample steps (compared to U-Net's four downsample steps). The output of the encoder shown in FIG. 9 is the latent representation with 16 channels. Instead of standard ReLU, LeakyRelu may be used as the activation layer in the encoders in order to prevent the optimization from getting trapped in local minima by preserving negative gradients. The input and output of the encoder were of same dimension in width and height. The number of channels of the encoder output may be, for example, 16, which produces produced good results while keeping the model small. In a similar fashion as an implementation of VAE, each model may be encoded by individual encoder before latent representation fusion.

The decoder, shown in FIG. 10, includes only two convolutional blocks and a 1×1 convolutional layer. In an example, the decoder is a fully convolutional network that decodes the fused latent representation and reconstructs the slice of interest in input volume. The decoder is constructed by two blocks of convolutional layers and activation layers. A skip connection may be established between the input and output of each block to enhance the gradient flow for backpropagation. The last 1×1 convolutional layer with an activational layer convert all channels to a single channel image of dimension H×W×1 as output.

Figure 11:
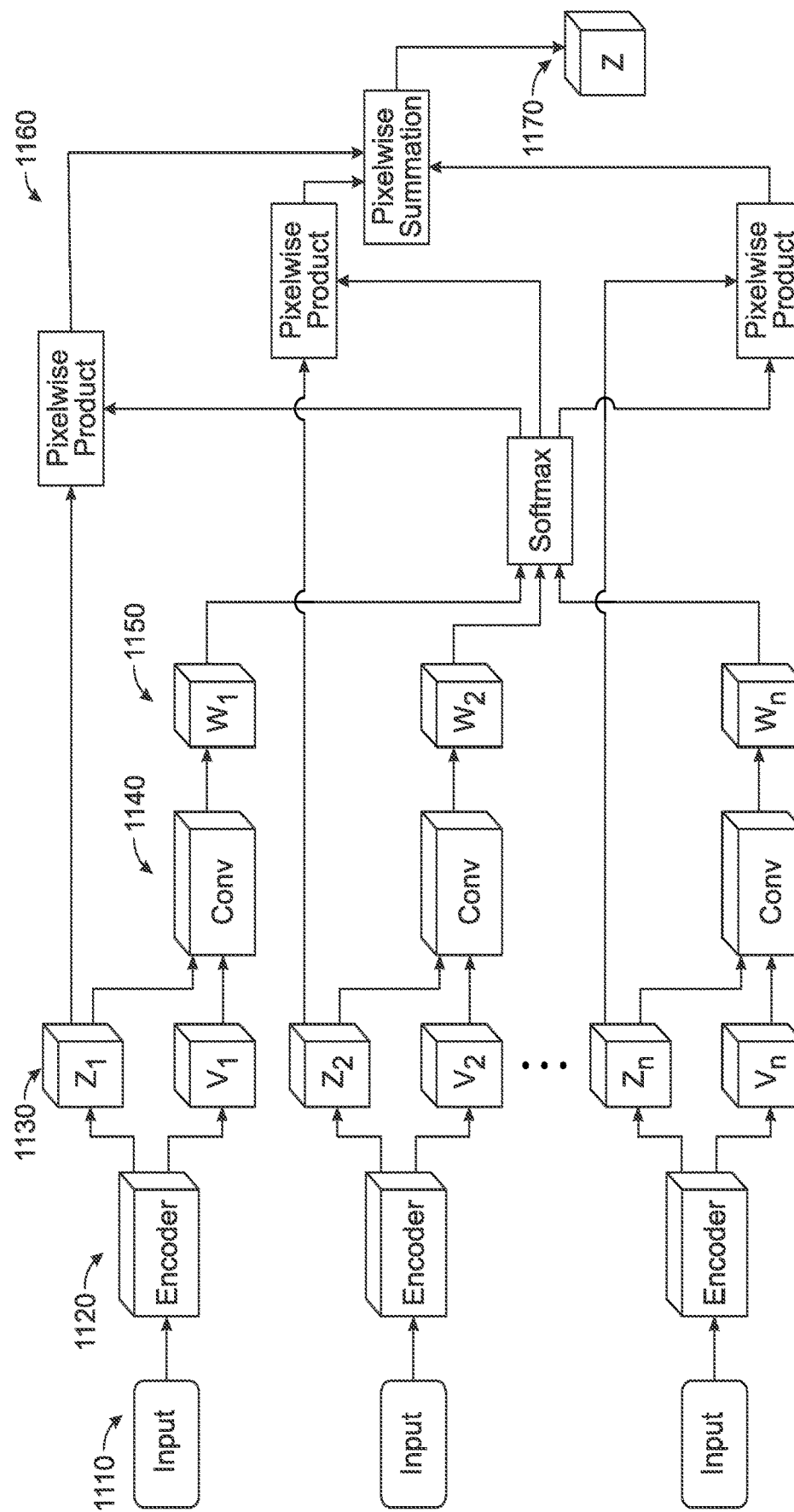
FIG. 11 illustrates a data flow diagram of a learning algorithm for a combined latent representation of respective imaging inputs.

After encoding to a unified representation, the fusion in a latent space may be performed using a number of different approaches, including taking the max, mean of latent vectors from all available models, or other algorithms. Latent learning may also be performed during the fusion. As an example, FIG. 11 illustrates a data flow diagram of a learning algorithm for a combined latent representation of respective imaging inputs. As shown, each encoder (1120) provides a latent vector and a weighting in order to fuse the latent representations (1130) by inner product. Each encoder (1120) outputs two components (1130) from the input (1110): a latent representation ($z_i$) and a variable ($v_i$). A pixelwise weighting (1160) of a latent representation (1150) for each model is learned with the latent vector and variable. The total sum of pixelwise weighting (1160) is a unit after a softmax activation. The fused latent representation (1170) accordingly is the inner product of the weightings and the latent representations.

The latent representations encoded should share similar features in the latent space before fusion, otherwise the fusion of latent vectors become meaningless. The similarity of latent variables thus may be maximized by minimizing the variance of latent vectors among all models, which contributes to the cost function. Different dimensions of latent space may be considered in the network in order to get the balance between memory use and the abstract of features.

Figure 12:
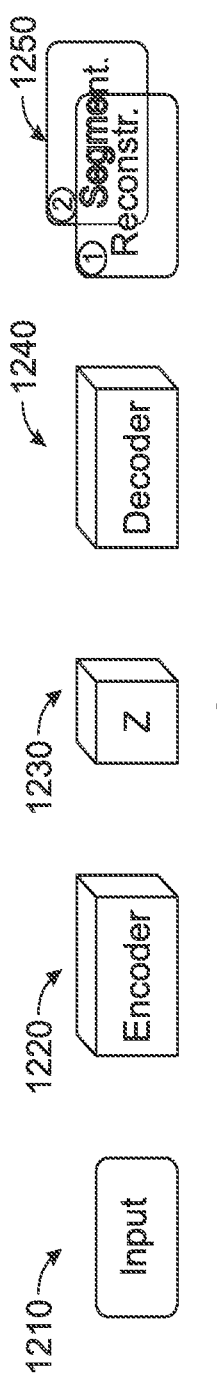
FIGS. 12 and 13 illustrate data flow architectures for segmentation image processing operations, in connection with use of a latent representation of an imaging input.
Figure 13:
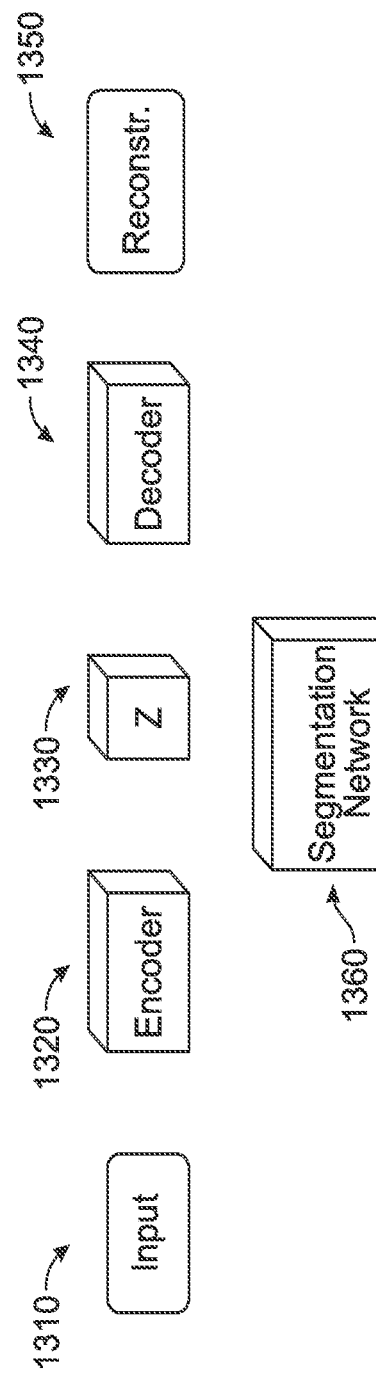

FIGS. 12 and 13 illustrate data flow architectures for segmentation image processing operations, in connection with use of a latent representation of an imaging input. In the fine-tuning model depicted in FIG. 12, the input (1210) can be converted by the encoder (1220) to a fused latent representation (1230), and can also be converted back by the decoder (1240). In this fine tuning model, however, the network for segmentation (1250) is the same for reconstruction (1250). The only difference is that the output is replaced by the ground truth of segmentation (or another image processing operation). The weightings learned from reconstruction optimization may be fine-tuned for segmentation with a lower learning rate.

In the joint training model depicted in FIG. 13, similar operations with input (1310) via an encoder (1320), a fused latent representation (1330), and a decoder (1340) can be used to perform reconstruction (1350). However, in this joint training model, an additional network (1360) is applied to the latent space to produce a segmentation result (1370). The network learns to reconstruct the input data and segment the item of interest (e.g., a tumor) during training.

Direct end-to-end segmentation often causes the optimization stuck at bad local minima. Output with all zeros developed early in the training. Besides, supervised segmentation training often needs great amount of labeled data to achieve good generalization. Thus, with a fine tuning approach, the network was first trained with reconstruction to allow extraction of features in hidden layers. The weightings at hidden layers were then fine-tuned by replacing the output with segmentation labels using lower learning rate to adjust the features for segmentation. The L2 reconstruction loss was also replaced by segmentation loss in the cost function. In fine-tuning, the network architecture does not change but only the cost function, output and weightings in the hidden layers.

Compared to fine-tuning, joint training allows an additional network for additional tasks, segmentation in this case. Joint training is often easier to train but it requires more use of memory. Reconstruction and segmentation were optimized at the same time, or consecutively during training. When two tasks were optimized by single optimizer, the weightings of each component (reconstruction and segmentation) in cost function comes into play in order to achieve a desired goal. Otherwise, joint training could also be achieved by using separated optimizer, (e.g., one optimizer learns to reconstruct the input data in order to learn the latent representation, while another optimizer undergoes another task). Joint training with multiple optimizers is simpler in training but the additional network would start being optimized only when the reconstruction reaches certain precision in order to ensure stable gradient descent optimization in segmentation.

Figure 14:
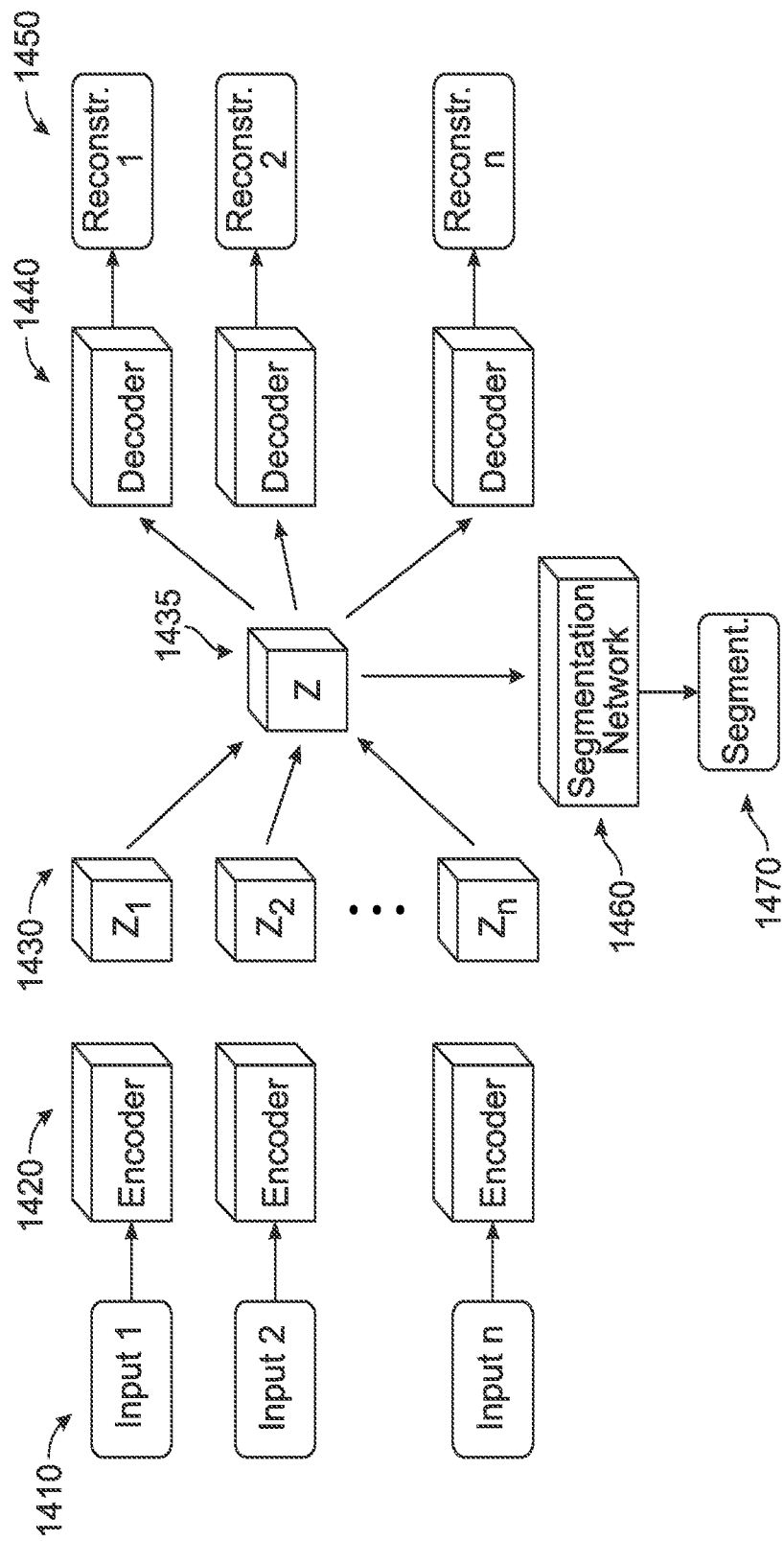
FIG. 14 illustrates a data flow architecture for segmentation image processing operations, in connection with joint training segmentation performed for a fused latent representation of an imaging input.

Accordingly, FIG. 14 illustrates a data flow architecture for segmentation image processing operations, in connection with joint training segmentation performed for a fused latent representation of an imaging input. Similar to the previously depicted models, input (1410) is encoded by an encoder (1420) into a latent representation (1430), and fused into the fused latent representation (1435); further operations of decoding may be performed by a decoder (1440) to result in a reconstruction (1450). In this example, however, the additional segmentation network (1460) has the fused latent representation as an input, and is trained to predict a segmentation result (1470) (e.g., a tumor segmentation) based upon the fused latent representation. As a result, during training, the latent representations are learned by reconstruction optimization.

Figure 15:
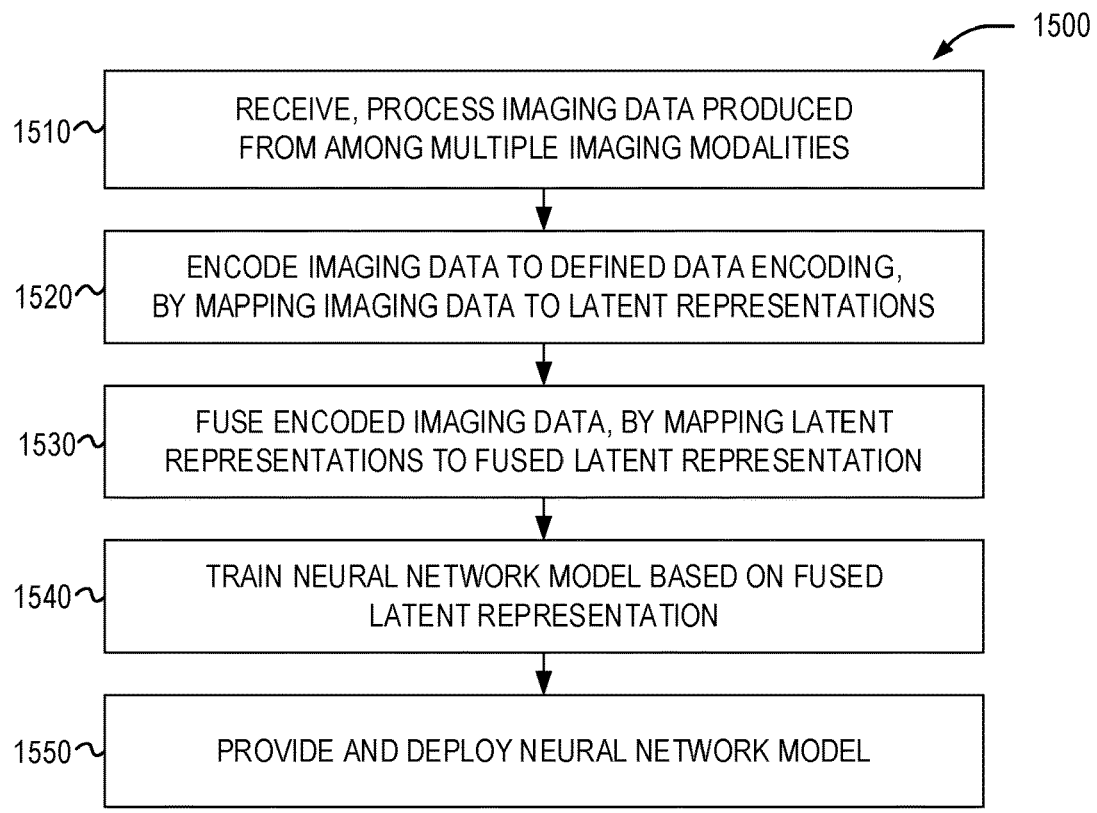
FIG. 15 illustrates a flowchart of exemplary operations for generating a modality-agnostic image processing model according to the presently disclosed techniques.

FIG. 15 illustrates a flowchart 1500 of exemplary operations for generating a modality-agnostic image processing model according to the presently disclosed techniques. It will be understood that the flowcharts depicted in FIGS. 15 and 16 may not include many details of the preceding mathematical and data processing operations for purposes of simplicity. As a result, additional or substitute operations may be integrated into the operations of flowchart 1500 (and flowchart 1600, further discussed below).

The flowchart 1500 begins with operations to obtain (e.g., receive, request, etc.) and process imaging data produced from among multiple imaging modalities (operation 1510). In an example, imaging data is captured by or from among the multiple imaging modalities, such that the respective sets of imaging data captured from among the multiple imaging modalities includes images produced from among a plurality of modality types or from a plurality of modes of at least one modality type.

The flowchart 1500 continues with operations to encode the imaging data based on a defined data encoding, by mapping the imaging data to respective latent representations (operation 1520). In an example, the encoding further produces confidence values corresponding to the respective latent representations, such that the confidence values are used as weights in mapping the respective latent representations into the fused latent representation. In a specific example, the encoding is performed with a variational autoencoder model trained for encoding of imaging data, and in a further example, the variational autoencoder model comprises a neural network. Also in an example, the defined data encoding is provided from among a plurality of encoders corresponding to a respective type or mode of the imaging modalities.

The flowchart 1500 continues with operations to fuse encoding imaging data from among the multiple imaging modalities (e.g., types of imaging modalities or modes of imaging operations), by mapping the respective latent representations to a fused latent representation of the encoded imaging data (operation 1530). In an example, the mapping conserves respective latent variables corresponding to a spatial representation of the respective latent representations. In a further example, the fused latent representation is produced as a fused representation image, and the following model training operations perform training using this fused representation image. For instance, the fused representation image may be produced using at least one of: spectral representations, covariance tapering, low rank approximations, or Gaussian Markov Random Fields. Also in a further example, fusing of the encoded imaging data applies respective weights corresponding to the plurality of encoders in producing the fused latent representation. The respective weights corresponding to the plurality of encoders may include normalized exponential confidence weights. Also in a further example, the fused latent representation includes a same number of image dimensions as included in the received (e.g., captured, obtained) imaging data.

The flowchart 1500 continues with the training of a model (such as a neural network model, although other types of models may be utilized) based on the fused latent representation (operation 1540). The flowchart 1500 concludes with operations that provide and deploy the model (operation 1550). For instance, the model may be the model adapted to produce an output (e.g., an inference, prediction, etc.) from subsequent medical imaging data, according to the training that is performed with the fused latent representation. Further operations may include obtaining (e.g. receiving, requesting) the subsequent medical imaging data that is provided from another modality type or imaging mode that was not trained (e.g., that was not included in the received imaging data used for training). The deployment of the model thus may include operating the trained model on the subsequent medical imaging data of the another modality type or imaging mode.

Figure 16:
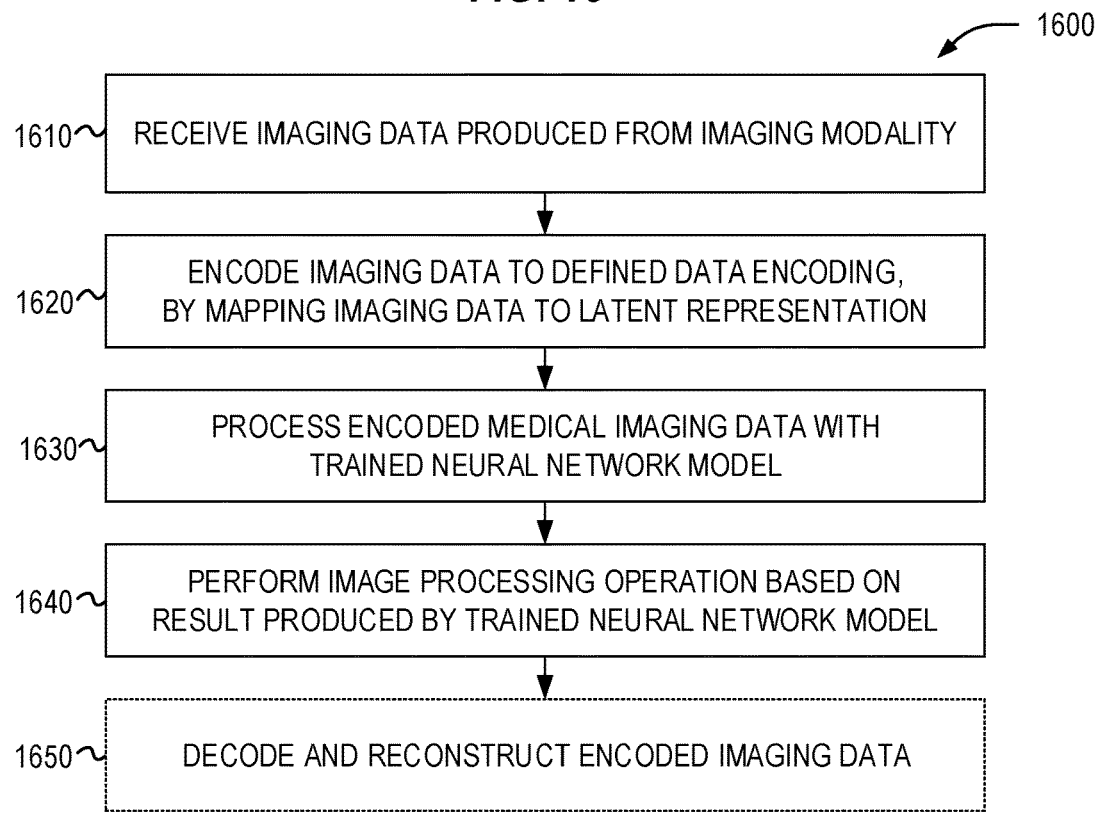
FIG. 16 illustrates a flowchart of exemplary operations for processing image data using a trained modality-agnostic image processing model according to the presently disclosed techniques.

FIG. 16 illustrates a flowchart 1600 of exemplary operations for processing image data using a trained modality-agnostic image processing model according to the presently disclosed techniques. The operations of flowchart 1600 may occur in a complimentary or combined fashion to those described with flowchart 1500, above; however, other types of training or model configuration may also be utilized with the following imaging data processing techniques.

The flowchart 1500 begins with operations to obtain (e.g., receive, request, etc.) and process imaging data produced from a particular medical imaging modality (operation 1610) of a particular imaging modality type or imaging modality mode. The flowchart 1500 follows with operations to encode the imaging data based on a defined data encoding (operation 1620), which maps the input medical imaging data to a latent representation. As discussed above, this encoding may involve the use of an encoder model, including a variational autoencoder. In a specific example, the variational autoencoder model comprises a neural network, and the variational autoencoder model is trained for encoding of imaging data, such that the latent representation is produced from spatial latent variables used in the variational autoencoder model.

The flowchart 1500 continues with operations to process the encoded medical imaging data with a trained model (operation 1630), such that the trained model produces an output based on the latent representation, based on training of the model to a fused latent representation of the imaging data, such as for a model having training performed based on a mapping of a latent representation from at least a second imaging modality. In an example, the first imaging modality comprises a first modality type or a first modality mode, the trained model is a neural network, and the trained model is trained using data from at least a second modality type or a second modality mode, such that the first modality type or first modality mode is unused in training the model.

Also in further examples, the first imaging modality and the second imaging modality are respective types of imaging procedures, comprising at least two of: Magnetic resonance imaging (MRI), computed tomography (CT), Positron Emission Tomography (PET), PET-CT, Ultrasound, X-Ray, Fluoroscopy, Single-photon emission computed tomography (SPECT), Elastography, Photoacoustic, Magnetoencephalography (MEG), or Electroencephalography (EEG) imaging procedures, or combinations of such imaging procedures. Also in a further example, the first imaging modality and the second imaging modality are respective types of MRI imaging modes, comprising at least two of T1, T1 with contrast, T2, PD, SSFP, STIR, FLAIR, DIR, DWI, PWI, or fMRI.

The flowchart 1600 continues with operations that perform an image processing operation (e.g., to produce an inference, prediction, classification, etc.) base don a result produced with the trained neural network model (operation 1640). In an example, this image processing operation is used as part of at least one of segmentation, denoising, synthesis, classification, regression, or reconstruction. The flowchart 1600 concludes with specific optional operations to decode and reconstruct the encoded imaging data (e.g., with a decoder model) (operation 1650).

As previously discussed, respective electronic computing systems or devices may implement one or more of the methods or functional operations as discussed herein. In various embodiments, such electronic computing systems or devices operates as a standalone device or may be connected (e.g., networked) to other machines. For instance, such computing systems or devices may operate in the capacity of a server or a client machine in server-client network environment, or as a peer machine in a peer-to-peer (or distributed) network environment. Features of computing systems or devices may be embodied by a personal computer (PC), a tablet PC, a Personal Digital Assistant (PDA), a cellular telephone, a web appliance, or any machine capable of executing instructions (sequential or otherwise) that specify actions to be taken by that machine.

As also indicated above, the functionality discussed above may be implemented by instructions, logic, or other information storage on a machine readable medium. While the machine-readable medium may have been described in various examples with reference to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions.

The above detailed description includes references to the accompanying drawings, which form a part of the detailed description. The drawings show, by way of illustration but not by way of limitation, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a," "an," "the," and "said" are used when introducing elements of aspects of the invention or in the embodiments thereof, as is common in patent documents, to include one or more than one or more of the elements, independent of any other instances or usages of "at least one" or "one or more." In this document, the term "or" is used to refer to a nonexclusive or, such that "A or B" includes "A but not B," "B but not A," and "A and B," unless otherwise indicated.

In the appended claims, the terms "including" and "in which" are used as the plain-English equivalents of the respective terms "comprising" and "wherein." Also, in the following claims, the terms "comprising," "including," and "having" are intended to be open-ended to mean that there may be additional elements other than the listed elements, such that after such a term (e.g., comprising, including, having) in a claim are still deemed to fall within the scope of that claim. Moreover, in the following claims, the terms "first," "second," and "third," etc., are used merely as labels, and are not intended to impose numerical requirements on their objects.

The present invention also relates to a computing system adapted, configured, or operated for performing the operations herein. This system may be specially constructed for the required purposes, or it may comprise a general purpose computer selectively activated or reconfigured by a computer program (e.g., instructions, code, etc.) stored in the computer. The order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In view of the above, it will be seen that the several objects of the invention are achieved and other advantageous results attained. Having described aspects of the invention in detail, it will be apparent that modifications and variations are possible without departing from the scope of aspects of the invention as defined in the appended claims. As various changes could be made in the above constructions, products, and methods without departing from the scope of aspects of the invention, it is intended that all matter contained in the above description and shown in the accompanying drawings shall be interpreted as illustrative and not in a limiting sense.

The above description is intended to be illustrative, and not restrictive. For example, the above-described examples (or one or more aspects thereof) may be used in combination with each other. In addition, many modifications may be made to adapt a particular situation or material to the teachings of the invention without departing from its scope. While the dimensions, types of materials and example parameters, functions, and implementations described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled.

Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. A computer implemented method for generating a modality-agnostic image processing model, the method comprising:
    receiving imaging data from multiple imaging modalities;
    encoding the imaging data based on applying a defined data encoding for each modality of the multiple imaging modalities, the encoding comprising:
        mapping the imaging data to respective latent representations corresponding to the multiple imaging modalities, and
        producing respective latent variables from applying the defined data encoding to the imaging data, wherein the respective latent variables correspond to a spatial representation of the respective latent representations;
    fusing the encoded imaging data, the fusing comprising:
        mapping the respective latent representations to a fused latent representation of the encoded imaging data,
        wherein the mapping uses the respective latent representations and the respective latent variables to determine the fused latent representation, and
        wherein the mapping combines the respective latent representations into the fused latent representation while conserving structure indicated by the respective latent variables;
    training a model for medical imaging processing, using the fused latent representation of the encoded imaging data; and
    outputting the trained model, the model adapted to produce an output from subsequent medical imaging data according to the training using the fused latent representation.

2. The method of claim 1, wherein the encoding further comprises producing confidence values corresponding to the respective latent representations, and wherein the confidence values are used as weights in mapping the respective latent representations into the fused latent representation.

3. The method of claim 1, wherein the encoding is performed with a variational autoencoder model.

4. The method of claim 3, wherein the variational autoencoder model comprises a neural network.

5. The method of claim 3, wherein the variational autoencoder model is trained for encoding of imaging data, and wherein the respective latent variables used in the fusing are produced from spatial latent variables used in the variational autoencoder model.

6. The method of claim 1, wherein respective sets of the imaging data are captured from among the multiple imaging modalities, wherein the respective sets of the imaging data captured from among the multiple imaging modalities includes images produced from among a plurality of modality types or from a plurality of modes of at least one modality type.

7. The method of claim 1, wherein the fused latent representation is produced as a fused representation image, and wherein the model is trained based on the fused representation image.

8. The method of claim 7, wherein the fused representation image is produced using at least one of: spectral representations, covariance tapering, low rank approximations, or Gaussian Markov Random Fields.

9. The method of claim 1, wherein the defined data encoding is provided from among a plurality of encoders corresponding to a respective type or mode of the imaging modalities.

10. The method of claim 9, wherein the fusing of the encoded imaging data applies respective weights corresponding to the plurality of encoders in producing the fused latent representation.

11. The method of claim 10, wherein the respective weights corresponding to the plurality of encoders are normalized exponential confidence weights.

12. The method of claim 1, wherein the fused latent representation includes a same number of image dimensions as included in the received imaging data.

13. The method of claim 1, further comprising,
receiving the subsequent medical imaging data, the subsequent medical imaging data provided from another modality type or mode that is not included in the received imaging data captured from multiple imaging modalities;
operating the trained model on the subsequent medical imaging data of the another modality type or mode.

14. The method of claim 1, wherein the output produced from operating the trained model is used for performing radiotherapy planning operations.

15. A computer-implemented method for processing imaging data using a trained modality-agnostic model, the method comprising:
receiving medical imaging data of a first imaging modality;
encoding the medical imaging data based on a defined data encoding, by mapping the medical imaging data to a latent representation;
processing the encoded medical imaging data with a trained model, wherein the trained model produces an output based on the latent representation, based on training of the model to a fused latent representation of training imaging data, wherein training of the model is performed based on a mapping of a latent representation of the training imaging data obtained from at least a second imaging modality, wherein the training of the model is performed from:
encoding of the training imaging data based on a defined data encoding for each modality of the training imaging data, the encoding performed from mapping of the training imaging data to respective latent representations corresponding to each modality, and producing respective latent variables from applying the defined data encoding to the training imaging data, wherein the respective latent variables correspond to a spatial representation of the respective latent representations; and
fusing of the encoded training imaging data, the fusing performed from mapping of the respective latent representations to a fused latent representation of the encoded training imaging data, wherein the mapping uses the respective latent representations and the respective latent variables to determine the fused latent representation, and wherein the mapping combines the respective latent representations into the fused latent representation while conserving structure indicated by the respective latent variables; and
performing an image processing operation on the medical imaging data based on the output produced by the trained model.

16. The method of claim 15, wherein the image processing operation comprises at least one of: segmentation, denoising, synthesis, classification, regression, or reconstruction.

17. The method of claim 15, the method further comprising:
decoding the encoded imaging data; and
performing image reconstruction based on the decoded imaging data.

18. The method of claim 17, wherein the first imaging modality comprises a first modality type or a first modality mode, wherein the trained model is a neural network, and wherein the trained model is trained using data from at least a second modality type or a second modality mode, and wherein the first modality type or first modality mode is unused in training the model.

19. The method of claim 17, wherein the first imaging modality and the second imaging modality are respective types of imaging procedures, comprising at least two of: Magnetic resonance imaging (MRI), computed tomography (CT), Positron Emission Tomography (PET), PET-CT, Ultrasound, X-Ray, Fluoroscopy, Single-photon emission computed tomography (SPECT), Elastography, Photoacoustic, Magnetoencephalography (MEG), or Electroencephalography (EEG) imaging procedures, or combinations of such imaging procedures.

20. The method of claim 19, wherein the first imaging modality and the second imaging modality are respective types of MRI imaging modes, comprising at least two of: T1, T1 with contrast, T2, PD, SSFP, STIR, FLAIR, DIR, DWI, PWI, or fMRI.

21. The method of claim 15, wherein the encoding is performed with a variational autoencoder model, wherein the variational autoencoder model comprises a neural network, wherein the variational autoencoder model is trained for encoding of imaging data, and wherein the latent representation is produced from spatial latent variables used in the variational autoencoder model.

22. A system for operation of a modality-agnostic imaging processing model, the system comprising:
processing circuitry comprising at least one processor; and
a storage medium comprising instructions, which when executed by the at least one processor, cause the processor to:
process imaging data produced from a medical imaging modality;
encode the imaging data to a latent representation based on a defined data encoding, wherein one or more latent variables are produced from applying the defined data encoding to the imaging data, and wherein the one or more latent variables correspond to a spatial representation of the latent representation;
perform mapping of the encoded imaging data to a common latent representation, wherein the mapping uses the latent representation and the one or more latent variables to determine the common latent representation, and wherein the mapping combines the latent representation into the common latent representation while conserving structure indicated by the one or more latent variables;
train a model for medical imaging processing, using the common latent representation; and
utilize the trained model to produce an output from subsequent medical imaging data, in connection with an image processing operation.

23. The system of claim 22, wherein the encoding further produces at least one confidence value corresponding to the latent representation, and wherein the confidence values are used as weights in mapping the latent representation into the common latent representation.

24. The system of claim 22, wherein the defined data encoding is performed with a variational autoencoder model, wherein the variational autoencoder model comprises a neural network, wherein the variational autoencoder model is trained for encoding of imaging data, and wherein the respective latent variables are produced from spatial latent variables used in the variational autoencoder model.

25. The system of claim 22, wherein the common latent representation is produced as a fused representation image from among multiple latent representations, wherein the model is trained based on the fused representation image, and wherein the fused representation image is produced using at least one of: spectral representations, covariance tapering, low rank approximations, or Gaussian Markov Random Fields.

26. The system of claim 22, wherein the imaging data is captured from one of multiple imaging modalities, wherein the common latent representation provides a fusion of latent representations from among the multiple imaging modalities, and wherein the multiple imaging modalities comprises modalities from among a plurality of modality types or from a plurality of modes of at least one modality type.

27. The system of claim 26, wherein the defined data encoding is provided from among a plurality of encoders corresponding to a respective type or mode of the multiple imaging modalities, and wherein the mapping of the encoded imaging data applies respective weights corresponding to the plurality of encoders in producing the common latent representation.

28. The system of claim 22, wherein utilizing the model occurs as part of performing radiotherapy planning operations based on the subsequent medical imaging data.

29. The system of claim 28, wherein the image processing operation comprises at least one of: segmentation, denoising, synthesis, classification, regression, or reconstruction.

30. The system of claim 22, wherein the imaging data is produced from at least one:
Magnetic resonance imaging (MRI), computed tomography (CT), Positron Emission Tomography (PET), PET-CT, Ultrasound, X-Ray, Fluoroscopy, Single-photon emission computed tomography (SPECT), Elastography, Photoacoustic, Magnetoencephalography (MEG), or Electroencephalography (EEG) imaging procedure, or combinations of such imaging procedures.

31. The system of claim 30, wherein the imaging procedure includes a MM imaging procedure that operates in at least one type of MRI imaging mode, wherein the MM imaging mode includes at least one of: T1, T1 with contrast, T2, PD, SSFP, STIR, FLAIR, DIR, DWI, PWI, or fMRI.

* * * * *

UNITED STATES PATENT AND TRADEMARK OFFICE
CERTIFICATE OF CORRECTION

PATENT NO. : 10,762,398 B2
APPLICATION NO. : 15/986065
DATED : September 1, 2020
INVENTOR(S) : Sjölund et al.

Page 1 of 1

It is certified that error appears in the above-identified patent and that said Letters Patent is hereby corrected as shown below:

In the Claims

In Column 34, Line 17, in Claim 31, delete "MM" and insert --MRI-- therefor

In Column 34, Line 18, in Claim 31, delete "MM" and insert --MRI-- therefor

Signed and Sealed this
Twenty-sixth Day of January, 2021

Drew Hirshfeld
*Performing the Functions and Duties of the
Under Secretary of Commerce for Intellectual Property and
Director of the United States Patent and Trademark Office*